(12) United States Patent
Reed et al.

(10) Patent No.: US 7,741,521 B2
(45) Date of Patent: Jun. 22, 2010

(54) INHIBITION OF BID-INDUCED CELL-DEATH USING SMALL ORGANIC MOLECULES

(75) Inventors: John C. Reed, Rancho Santa Fe, CA (US); Maurizio Pellecchia, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 720 days.

(21) Appl. No.: 11/645,239

(22) Filed: Dec. 22, 2006

(65) Prior Publication Data

US 2007/0185196 A1 Aug. 9, 2007

Related U.S. Application Data

(63) Continuation-in-part of application No. PCT/US2005/022640, filed on Jun. 27, 2005.

(60) Provisional application No. 60/583,189, filed on Jun. 25, 2004.

(51) Int. Cl.
*C07C 233/05* (2006.01)
*C07C 233/65* (2006.01)
*A61K 31/16* (2006.01)

(52) U.S. Cl. .......... 564/154; 564/84; 564/194; 514/604; 514/616; 514/626

(58) Field of Classification Search ............... 514/604, 514/616, 626; 564/84, 154, 194
See application file for complete search history.

(56) References Cited

FOREIGN PATENT DOCUMENTS

EP 0 183 271 A2 6/1986

OTHER PUBLICATIONS

Becattini et al, Chemistry & Biology, vol. 11, 2004, 1107-1117.*
Abbady et al., Synthesis & Biological Activity of some New Diaryl Sulfides & Diaryl Sulphones containing Amino acid Moieties, Indian Journal of Chemistry, 20B;53-57, 1980.

* cited by examiner

*Primary Examiner*—Shailendra Kumar
(74) *Attorney, Agent, or Firm*—DLA Piper LLP (US)

(57) ABSTRACT

Various phenylamine derivatives are described as well as the use of compounds to inhibit BID protein for controlling apoptotic cascade.

8 Claims, 12 Drawing Sheets

INHIBITION OF BID-INDUCED CELL-DEATH USING SMALL ORGANIC MOLECULES

CROSS REFERENCE TO RELATED APPLICATIONS

This is a continuation-in-part application of PCT Application No. PCT/US2005/022640 filed Jun. 27, 2005, which claims the benefit under 35 USC §119(e) to U.S. application Ser. No. 60/583,189 filed Jun. 25, 2004. The disclosure of the prior applications is considered part of and is incorporated by reference in the disclosure of this application.

GRANT INFORMATION

The invention was made in part with government support under Grant Nos. HG01642 and 5T32-GM07616 awarded by the National Institutes of Health, CA78040, and CA30199-22, awarded by the National Institute of Health. The United States Government has certain rights in the invention.

BACKGROUND OF THE INVENTION

1. Field of the Invention

The present invention relates generally to the use of compounds to treat a variety of disorders, diseases and pathologic conditions and more specifically to the use of phenylamine derivatives to treat various disorders.

2. Background Information

Currently, there is a need for compounds that are capable of selectively killing and/or reducing the viability of various cells. There is also a need for pharmacological tools for the further study of the physiological processes associated with apoptosis.

The apoptotic cascade in cells is known to lead to cell death. Uncontrolled cell death can be associated with several human pathologies, such as neurodegenerative diseases, ALS, liver inflammation, multiple sclerosis, and ischemic injuries. BH3 Interacting Domain Death Antagonist (BID) is a protein that is a member of the BCL-2 family proteins involved in the control of the apoptotic cascade. Therefore, BID represents a potential target for inhibition by various therapeutic agents. It is desirable that such therapeutic agents be capable of occupying a deep hydrophobic crevice on the surface of BID. Unfortunately, no such therapeutic agents have been developed.

Accordingly, a need exists to identify potent cell permeable compounds for targeting the BCL-2 family of receptors such as, for example, BCL-$x_L$, BCL-2, MCL-1, or BCL-B. There exists a need for agonists that can inhibit the binding of BH3 to the BCL-2 receptors.

In addition a need exists for compounds useful as chemosensitizers in particular, where anti-apoptotic BCL-2 family proteins, such as BCL-$x_L$, BCL-2, Mcl-1, BCL-W, or BCL-B, are overproduced by the cells.

SUMMARY OF THE INVENTION

The present invention provides for fragment-based designing of certain chemical compounds such as BID-inhibitors, and for methods of use thereof for treatment of various diseases, disorders, and pathologies, for example, various kinds of neurodegenerative diseases, liver inflammation, multiple sclerosis, heart disease, ischemic injury and other diseases where BID has been implicated. As shown by the schematic representation of death receptor activation (FIG. 1A), apoptosis usually occurs after being induced by caspase-8 mediated BID activation. However, using compounds capable of blocking BID migration, such as compound II described below, can result in cell survival (FIG. 1B).

The compounds described in this invention, such as 4-phenylsulfanyl-phenylamine derivatives, may be beneficial for treatment of the diseases where the treatment includes inhibition of BID, modulating caspase activity, and protection against cell death.

According to one embodiment of the invention, compounds having structure A, or a pharmaceutically acceptable salt thereof, are provided:

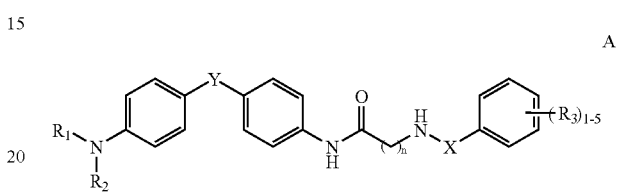

A

According to another embodiment of the invention, compounds having structure B, or a pharmaceutically acceptable salt thereof, are provided:

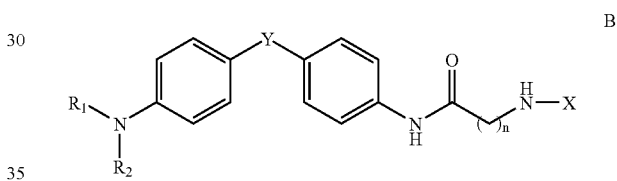

B

According to another embodiment of the invention, compounds having structure C, or a pharmaceutically acceptable salt thereof, are provided:

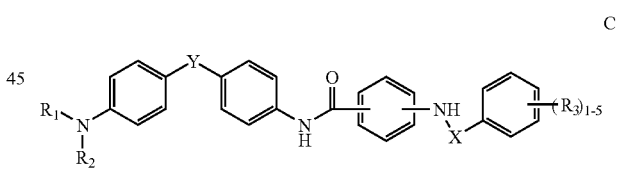

C

In each of the structures A and B shown above, each of $R_1$ and $R_2$ is independently selected from a group consisting of:

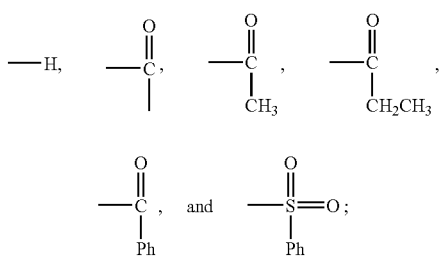

Y is a moiety selected from a group consisting of:

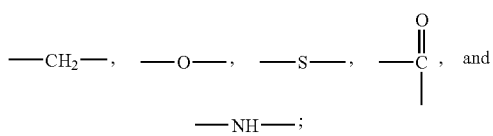

$R_3$ includes at least one substitutent in ortho-, meta-, or para-position of the benzene ring, wherein "$(R_3)_{1-5}$" symbolizes that the number of $R_3$ substitutents can be between 1 and 5, inclusively, and can be is selected from a group consisting of:

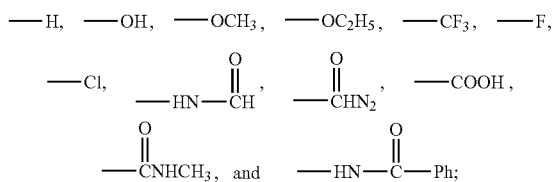

n is an integer having the value between 1 and 5; and

Ph in any of $R_1$, $R_2$, and $R_3$ can be independently selected from an unsubstituted phenyl ring and a substituted phenyl ring having between one and five substitutents in ortho-, meta-, or para-position of the benzene ring, wherein the substitutents in the ring are selected from the group consisting of:

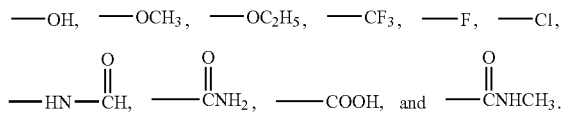

In each of the structures A and C shown above, X is a moiety selected from a group consisting of:

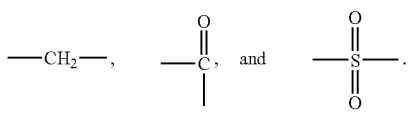

In the structure B shown above, X is a moiety selected from a group consisting of:

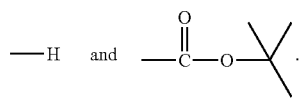

According to another embodiment of the present invention, a method for treating a disorder is provided, including administering to a subject in need thereof a therapeutically effective amount of at least one compound A, B, or C, as described above, or pharmaceutically acceptable salts, hydrates, or solvates of such compound(s). The disorder or disease that is treated is associated with cell death. The mode of treatment may include inhibition of BID, modulating caspase activity, and protection against cell death. The disorder or disease includes various kinds of neurodegenerative diseases (e.g., Alzheimer's disease, Parkinson's disease, a polyglutamine-repeat disorder, Huntington's disease, multiple sclerosis, amyotrophic lateral sclerosis, or Down's syndrome), heart disease, liver inflammation, cerebral injury, ischemic injury, myocardial infarction, sepsis, liver failure, spinal cord injury or BID-implicated diseases. As shown by FIG. 1, BID plays a central role in the apoptotic machinery mediating cytochrome c and SMAC/DIABLO release from mitochondria, an event for caspase activation and cell-death (FIG. 1).

According to another embodiment of the present invention, an article of manufacture is provided, comprising packaging material and a pharmaceutical composition contained with the packaging material, wherein the packaging material comprises a label which indicates that the pharmaceutical composition can be used for treatment of disorders associated with uncontrolled cell death, and wherein the pharmaceutical composition comprises at least one compound A, B, or C, as described above, and a pharmaceutically acceptable carrier therefor.

According to another embodiment of the present invention, an article of manufacture is provided, comprising packaging material and a pharmaceutical composition contained with the packaging material, wherein the packaging material comprises a label which indicates that the pharmaceutical composition can be used for treatment of disorders selected from various kinds of neurodegenerative diseases (e.g., Alzheimer's disease, Parkinson's disease, a polyglutamine-repeat disorder, Huntington's disease, multiple sclerosis, amyotrophic lateral sclerosis, or Down's syndrome), heart disease, liver inflammation, cerebral injury, ischemic injury, myocardial infarction, sepsis, liver failure, spinal cord injury or BID-implicated diseases, and wherein the pharmaceutical composition comprises at least one compound A, B, or C, as described above, and a pharmaceutically acceptable carrier therefor.

DETAILED DESCRIPTION OF THE INVENTION

Figure 1:
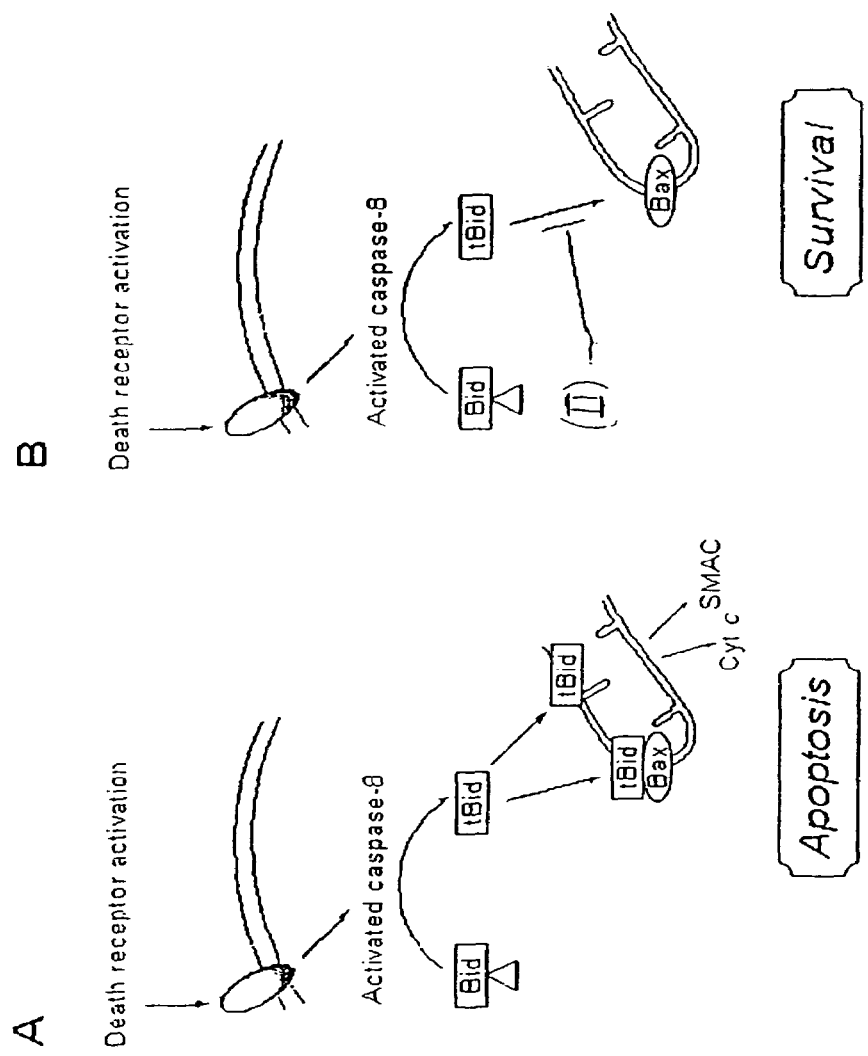
FIG. 1 is a scheme illustrating the process of cell death induced by BID.

The following terms, definitions and abbreviations apply:

The general terms "alkyl," "alkoxy," "alkenyl," and "alkynyl" refer to both straight-chain and branched groups; references to individual radicals include specifically either straight-chain or branched groups, but not both. For instance, a reference to "propyl" includes only the straight-chain radical while a reference to "isopropyl" includes only the branched group.

The term "alkyl" refers to a monovalent straight or branched chain hydrocarbon group. Examples of alkyl structures that can be used include $(C_1-C_6)$alkyls such as be methyl, ethyl, propyl, isopropyl, butyl, isobutyl, sec-butyl, tert-butyl, pentyl, 3-pentyl, or hexyl.

The term "halo" refers herein to fluoro, chloro, bromo, or iodo. The term "haloalkyl" refers to a halogen substituted alkyl, such as halo$(C_1-C_6)$alkyl, for example, iodomethyl, bromomethyl, chloromethyl, fluoromethyl, trifluoromethyl, 2-chloroethyl, 2-fluoroethyl, 2,2,2-trifluoroethyl, or pentafluoroethyl.

The term "hydroxyalkyl" refers to a hydroxyl group-substituted alkyl, such as hydroxy$(C_1-C_6)$alkyl, for example, hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl The term "alkoxy" refers to the moiety —O-alkyl, wherein alkyl is as defined above. Examples of alkoxy structures that can be used include $(C_1-C_6)$alkoxy radicals, such as methoxy, ethoxy, propoxy, isopropoxy, butoxy, iso-butoxy, sec-butoxy, tert-butoxy, pentoxy, 3-pentoxy, or hexyloxy.

The term "alkylthio" refers to the moiety —S-alkyl, wherein alkyl is as defined above. Examples of alkylthio structures that can be used include $(C_1-C_6)$alkylthio moieties, such as methylthio, ethylthio, propylthio, isopropylthio, butylthio, isobutylthio, pentylthio, or hexylthio.

The term "aryl" refers to a phenyl radical or an ortho-fused bicyclic carbocyclic radical having about nine to ten ring atoms in which at least one ring is aromatic. Some examples of aryls that can be used include phenyl, indenyl, or naphthyl.

The term "amino acid" is defined to comprise the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, -methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an -methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The abbreviation "SAR" refers to "structure activity relationships." The abbreviation "ILOE" referes to "interligand nuclear Overhauser effect."

The term "patient" refers to organisms to be treated by the methods of the present invention. Such organisms include, but are not limited to, humans. In the context of the invention, the term "subject" generally refers to an individual who will receive or who has received treatment described below (e.g., administration of the compounds of the invention, and optionally one or more additional therapeutic agents).

According to an embodiment of the invention, by using SAR by ILOE approach, i.e., by screening a small but diverse library of compounds using NMR, that permits identification of pairs of small molecules that sit in adjacent sites on a surface of a given protein, it has been determined that compounds having the structures A, B, or C, shown below, or pharmaceutically acceptable salts, hydrates, or solvates thereof, are suitable for treatment of various diseases, disorders, and pathologies, due to their ability to bind simultaneously to a hydrophobic crevice on the surface of BID.

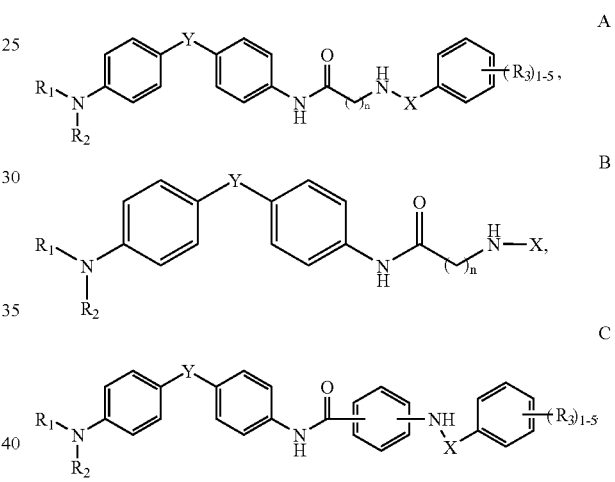

In structure A, each of $R_1$ and $R_2$ is independently selected from a group consisting of:

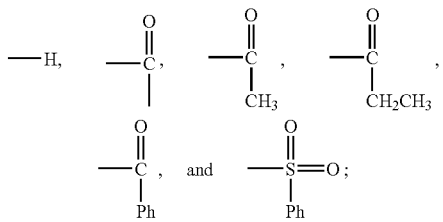

Y is a moiety selected from a group consisting of:

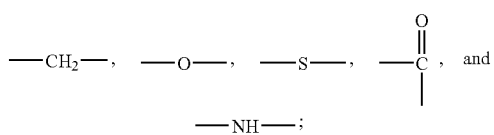

X is a moiety selected from a group consisting of:

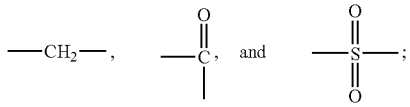

R₃ is at least one substitutent in ortho-, meta-, or para-position of the benzene ring, wherein "$(R_3)_{1-5}$" symbolizes that the number of R₃ substitutents is between 1 and 5, inclusively, wherein R₃ is selected from a group consisting of:

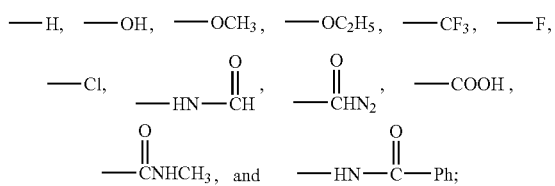

n is an integer having the value between 1 and 5; and

Ph in any of R₁, R₂, and R₃ is independently selected from an unsubstituted phenyl ring and a substituted phenyl ring having between one and five substitutents in ortho-, meta-, or para-position of the benzene ring, wherein the substitutents in the ring is selected from the group consisting of:

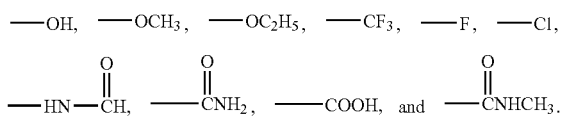

Some exemplary compounds described by structure A that can be used include compounds I through V shown below:

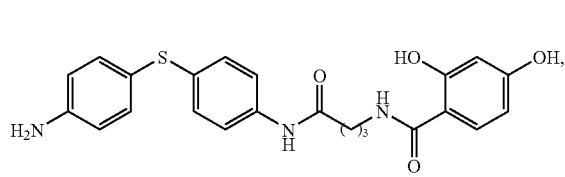

I

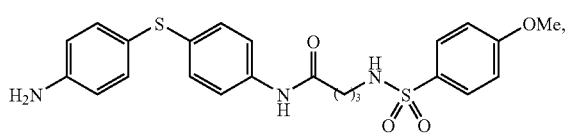

II

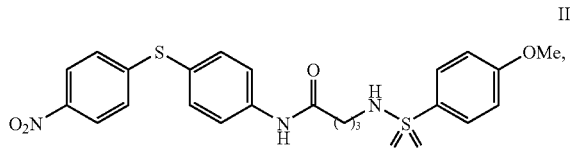

III

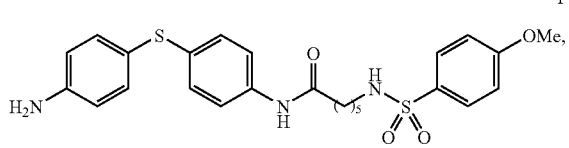

IV

-continued

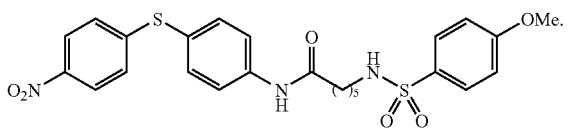

V

In structure B, each of R₁ and R₂ is independently selected from a group consisting of:

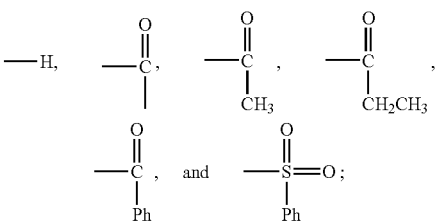

Y is a moiety selected from a group consisting of:

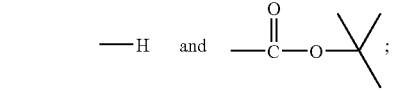

X is a moiety selected from a group consisting of:

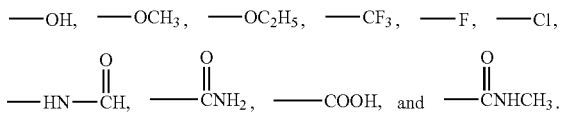

n is an integer having the value between 1 and 5; and

Ph in any of R₁ and R₂ is independently selected from an unsubstituted phenyl ring and a substituted phenyl ring having between one and five substitutents in ortho-, meta-, or para-position of the benzene ring, wherein the substitutents in the ring is selected from the group consisting of:

—OH, —OCH₃, —OC₂H₅, —CF₃, —F, —Cl, —HN—CH(=O), —CNH₂(=O), —COOH, and —CNHCH₃(=O).

Some exemplary compounds described by structure (B) that can be used include compounds VI through IX shown below:

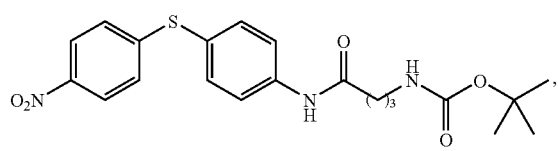

VI

-continued

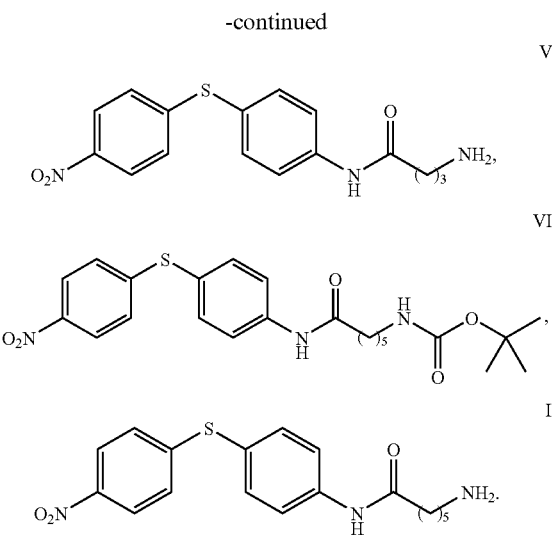

In structure C, each of $R_1$ and $R_2$ is independently selected from a group consisting of:

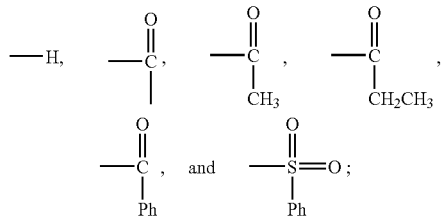

Y is a moiety selected from a group consisting of:

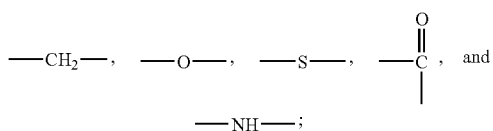

X is a moiety selected from a group consisting of:

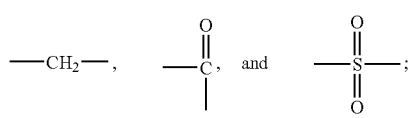

$R_3$ is at least one substituent in ortho-, meta-, or para-position of the benzene ring, wherein "$(R_3)_{1\text{-}5}$" symbolizes that the number of $R_3$ substitutents is between 1 and 5, inclusively, wherein $R_3$ is selected from a group consisting of:

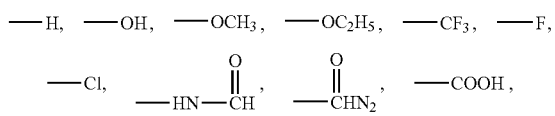

-continued

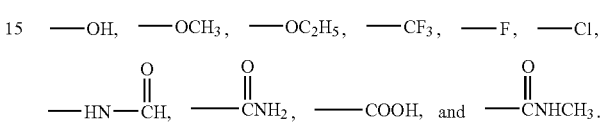

n is an integer having the value between 1 and 5; and

Ph in any of $R_1$, $R_2$, and $R_3$ is independently selected from an unsubstituted phenyl ring and a substituted phenyl ring having between one and five substitutents in ortho-, meta-, or para-position of the benzene ring, wherein the substitutents in the ring is selected from the group consisting of:

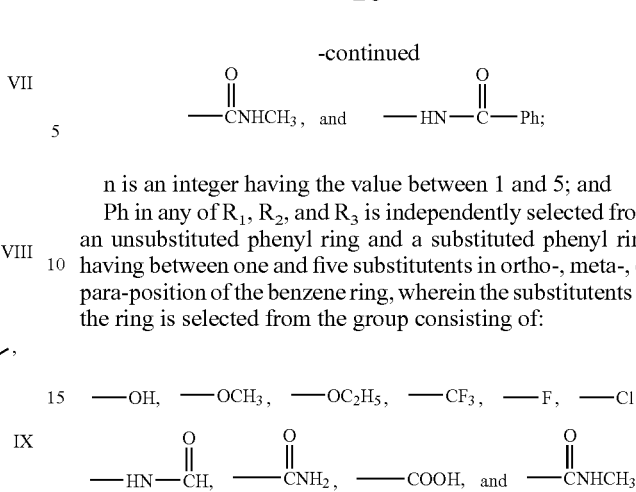

The synthetic routes used for the preparation of compounds I-IX are shown generally on FIGS. 7 and 5A, and the synthesis and results are further described in the "Examples" portion of the application below.

In some embodiments, some compounds of the invention may have a chiral center and can be isolated in optically active and racemic forms. Some compounds may exhibit polymorphism. The compounds of the present invention include any racemic, optically-active, polymorphic, or stereoisomeric form, or mixtures thereof, which possess the useful properties described herein. If desired, optically active forms can be prepared using commonly known techniques, e.g., by resolution of the racemic form by recrystallization techniques, by synthesis from optically-active starting materials, by chiral synthesis, or by chromatographic separation using a chiral stationary phase.

In certain embodiments, the inventive compounds are inhibitors of apoptotic proteins and are useful for the treatment of disorders resulting from excessive apoptotic activity. In one embodiment, the compounds inhibit BID protein.

In one embodiment, a method is provided for modulating the formation of complexes between BCL-2 proteins (such as BCL-$x_L$, BCL-2, Mcl-1, BCL-W, and BCL-B), and the BH3 domain of pro-apoptotic BCL-2 family members and compounds that are useful for modulating the amount or stability of these complexes. The method can include contacting BCL-2 with BH3 under conditions suitable to form a BCL-2-BH3 complex, and contacting the BCL-2-BH3 complex with any compound A, B, or C described above.

According to another embodiment, a method is provided for identifying compounds that can effectively modulate the binding of the BCL-2 family proteins (e.g., BCL-$x_L$, BCL-2, Mcl-1, BCL-W, and BCL-B) to BH3. The method can include contacting BCL-$X_L$ with BH3 under conditions suitable to form a BCL-$X_L$-BH3 complex, contacting the BCL-$X_L$-BH3 complex with a test compound, which can be any compound A, B, or C described above, and determining the ability of the test compound to modulate the binding of BCL-$X_L$ to BH3, where modulation of the binding of BCL-$X_L$ to BH3 indicates that the test compound is an effective compound that modulates the binding of BCL-$X_L$ to BH3.

In another embodiment, a method is provided for screening compounds using spectral techniques to determine the ability of the compounds of the invention to bind to the anti-apoptotic protein BCL-xL. The method can be used for screening various compounds such as green and black tea polyphenol compounds, by using a combination of Nuclear Magnetic Resonance (NMR) binding assays, Fluorescence Polarization Assay (FPA) and Computational-Docking studies.

In another embodiment, a method is provided for binding any compound A, B, or C described above to designated nicotine receptor sites, in vivo or in vitro, using an amount of any compound A, B, or C effective to bind to such receptors. Tissue comprising ligand bound designated nicotine receptor sites can be used to measure the selectivity of test compounds for specific receptor subtypes, or can be used as a tool to identify potential therapeutic agents for the treatment of diseases or conditions associated with acetyl choline disfunction, by contacting said agents with said ligand-receptor complexes, and measuring the extent of displacement of the ligand and/or binding of the agent.

According to other embodiments, a method is provided for treating neurodegenerative diseases, sepsis, liver failure, liver inflammation, spinal cord injury, heart disease, and ischemic injury. The method can include administering to a subject in need of such treatment, an effective amount of any compound A, B, or C described above, or pharmaceutically acceptable salts, hydrates, or solvates thereof. Non-limiting examples of the neurodegenerative diseases that can be treated include Alzheimer's disease, Parkinson's disease, polyglutamine-repeat disorders such as Huntington's disease, Down's syndrome, and multiple sclerosis.

According to another embodiment, any compound A, B, or C described above, can be used for the manufacture of a medicament for the treatment of a pathological condition or symptom in a mammal, such as a human. The medicament can be directed to the treatment of any pathology or condition described above.

According to another embodiment, pharmaceutical compositions are provided, the pharmaceutical compositions comprising any compound A, B, or C described above, or pharmaceutically acceptable salts, hydrates, or solvates thereof, and a pharmaceutically acceptable diluent or carrier. The pharmaceutical compositions can be used to treat any pathology or condition described above. The pharmaceutical compositions can further optionally include one or more additional therapeutic compounds.

In cases where the compounds A, B, or C are sufficiently basic or acidic to form stable nontoxic acid or base salts, administration of the compounds as salts may be appropriate. Examples of pharmaceutically acceptable salts include organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any tablets, troches, pills, capsules, and the like, which incorporate the inventive compounds, may also contain binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When there is a unit dosage form of the inventive compound in a capsule, it may contain, in addition to materials of the above type, a liquid carrier, such as a vegetable oil or a polyethylene glycol. Various other materials may be present as coatings or to otherwise modify the physical form of a solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compounds of the present invention may also be administered intravenously or intraperitoneally by infusion or injection. Solutions of the compounds or salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations may contain a preservative to prevent the growth of microorganisms.

Sterile injectable solutions can be prepared by incorporating the compounds of the present invention in the sufficient therapeutic amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user, as known to those having ordinary skill in the art.

Embodiments of the present invention can be further illustrated by the following non-limiting examples.

Example 1

General Materials and Methods

Library Design.

A library design approach was used. The NMR compound library was composed of about 300 low molecular weight compounds representing diverse core structures. This library was assembled and individual 1D $^1$H spectra were measured in D$_2$O buffer as control of compound purity, stability, and solubility in water buffer. The compounds having reactive functional groups such as halides, anhydrides, epoxides, aziridines, phosphonates and sulphonates esters, imines, aldehydes, Michael acceptors, halopyrimidines, were not included in the library. The following criteria were adopted for selection of the compounds for the library: average molecular weight was less than 300 Daltons; octanol/water repartition coefficient (LogP) was less than 1.3; number of rotatable bonds was between 0 and 2. The library was designed to optimize the detection of trNOEs and ILOEs by selecting compounds with appropriate derivatization of functional groups with proton NMR-detectable substituents.

Protein Expression and Purification.

Recombinant full length mouse BID was produced from a pET-19b (Novagen) plasmid construct containing the entire nucleotide sequence for BID fused to an N-terminal poly-His tag. Unlabeled BID was expressed in E. coli BL21 in LB media at 37° C., with an induction period of 3-4 hours with 1 mM IPTG. $^{15}$N-labeled BID was similarly produced, with growth occurring in M9 media supplemented with 0.5 g/L $^{15}$NH$_4$Cl. ε-$^{13}$C-Met labeled BID was produced in M9 media supplemented with 50 mg/L of ε-$^{13}$C-Met at time of induction with IPTG. Following cell lysis, soluble BID was purified over a Hi-Trap chelating column (Amersham, Pharmacia), followed by ion-exchange purification with a MonoQ (Amersham, Pharmacia) column. Final BID samples were dialyzed into a buffer appropriate for the subsequent experiments. tBID was produced by cleavage of purified BID with caspase-8, as known in the art.

Molecular Modeling.

Molecular modeling studies were conducted on several R12000 SGI Octane workstations with the software package Sybyl version 6.9 (TRIPOS). The docked structures of the compounds were initially obtained by FlexX as implemented in Sybyl. Molecular models of compounds were energy-minimized with MAXIMN2 (Sybyl). For each molecule, 20 solutions were generated and ranked according to CSCORE. The solutions were finally ranked by visual inspection of the linked compounds in the deep hydrophobic groove on the surface of BID. Surface representations were generated by MOLCAD.

NMR Spectroscopy (SAR by ILOEs).

For all NMR experiments, BID was exchanged into 50 mM phosphate buffer at pH 7.5 and measurements were performed at 30° C. 2D [$^{15}$N,$^1$H]-TROSY spectra for BID were measured with 0.5 mM samples of $^{15}$N-labeled BID. 2D [$^{13}$C,$^1$H]-HSQC spectra were measured with 0.2 mM samples of ε-$^{13}$C-Met labeled BID. 2D [$^1$H,$^1$H]-NOESY spectra were acquired with small molecules at a concentration of 0.9 mM in the presence of 10 μM BID. T$_{1\rho}$ competition experiments (200 msec spin-lock duration) were performed on either 100 μM BI-2A7 or a mixture of 100 μM BI-2A7 and 10 μM BI-6C9, in the presence and absence of 10 μM BID. All experiments were performed with either a 500 MHz or 600 MHz Bruker Avance spectrometer, both equipped with TXI probes. Typical parameters for the 2D [$^{15}$N,$^1$H]-TROSY spectra included $^1$H and $^{15}$N π/2 pulse lengths of 11 μsec and 40 μsec, respectively; $^1$H and $^{15}$N sweep widths of 12 ppm and 32 ppm, respectively; 16 scans and 256 indirect acquisition points and a recycle delay of 1 sec. For the 2D [$^{13}$C,$^1$H]-HSQC typical parameters included $^1$H and $^{13}$C π/2 pulse lengths of 10 μsec and 13 μsec, respectively; $^1$H and $^{13}$C sweep widths of 12 ppm and 5 ppm, respectively; 128 scans and 80 indirect acquisition points and a recycle delay of 1 sec.

2D [$^1$H,$^1$H]-NOESY spectra were typically acquired with 8 scans for each of 400 indirect points, a $^1$H π/2 pulse length of 11 μsec, sweep widths of 12 ppm in both dimensions, mixing times of 300-800 msec and a recycle delay of 1 sec. In all experiments, dephasing of residual water signals was obtained with a WATERGATE sequence.

Experiments with Isolated Mitochondria.

100 ng of tBID (cleaved by caspase 8) was pre-incubated with various concentrations of compounds for 15 minutes at 30° C. in HM buffer (10 mM Hepes, pH 7.4, 250 mM Mannitol, 10 mM KCl, 1.5 mM MgCl, 1 mM DTT, 1 mM EGTA), then 50 μg of isolated mitochondria from HCT116 cells were added to a final volume of 50 μl in HM buffer. After 1 hour incubation at 30° C., the samples were centrifuged at 10,000×g for 5 minutes at 4° C. and the supernatant was analyzed by SDS-PAGE/immunoblotting using anti-SMAC antibody.

Cell-Based Assays.

HEK 293T cells were transfected with 0.5 μg of plasmids encoding either GFP or GFP-tBID in 12 wells plate. After 3 hours transfection, various compounds were added in DMSO to the media. After 20 hours of further incubation, cells were collected and either lysed for caspase assays or fixed and stained with DAPI for determination of apoptosis[50]. For caspase activity assays, 293T cells were lysed in lysis buffer (10 mM Hepes, pH 7.4, 142.2 mM KCl, 5 mM MgCl$_2$, 0.5 mM EDTD, 0.5% NP-40) containing a protease inhibitor mixture (Roche Molecular Biochemicals). The lysates were normalized for protein concentration (10 μg), then incubated with 100 μM DEVD-AFC. Enzyme activity was determined by the release of AFC-fluorescence and V$_{max}$ was calculated (mean±Std. dev; n=3). For DAPI staining, 293T cells were fixed, washed with PBS, and stained with 0.1 mg/ml DAPI. The percentage of GFP-positive cells with apoptotic morphology (fragment nuclei or condensed chromatin) was determined (mean±Std. dev; n=3).

Experiments with Primary Neuronal Cells.

Primary cultures were obtained from embryonic day 18 rats and cultured in Neurobasal medium (Invitrogen, Karlsruhe, Germany) supplemented with 5 mM HEPES, 1.2 mM glutamine, B27 supplement (Invitrogen, 20 ml/l) and gentamicin (0.1 mg/ml) as described in the art. Glutamate (20 μM) was added in 9-10 day old cultures in EBSS medium (6800 mg/L NaCl, 400 mg/L KCl, 264 mg/L CaCl$_2$×2H$_2$O, 200 mg/L MgCl$_2$×7H$_2$O, 2200 mg/L NaHCO$_3$, 140 mg/L NaH$_2$PO$_4$×H$_2$O, 10 mM glucose, pH 7.2).

Neuronal cell death was quantified after staining the nuclei with the DNA-binding fluorochrome Hoechst 33258 (Molecular Probes) or by the MTT assay. Immunocytochemistry was performed as described in the art, with a polyclonal anti-AIF antibody (sc-9416, Santa Cruz; 1:200) followed by incubation a biotinylated anti-goat IgG antibody (1:200) Vector Laboratories) and Oregon Green-streptavidin (Molecular Probes). After counterstaining with Hoechst 33342 images were acquired using a confocal laser scanning microscope (Axiovert, Zeiss) with a 60× oil immersion objective (514-nm excitation and 535-nm emission for detection of Oregon Green and 352-nm excitation and 460-nm emission for detection of Hoechst 33342).

Example 2

Synthesis of N-((4-(4-aminophenylthio)phenylcarbamoyl)methyl)-2,4-dihydroxybenzamide (Compound I)

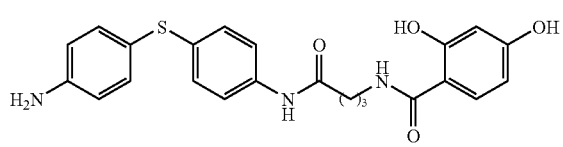

I

Figure 5:
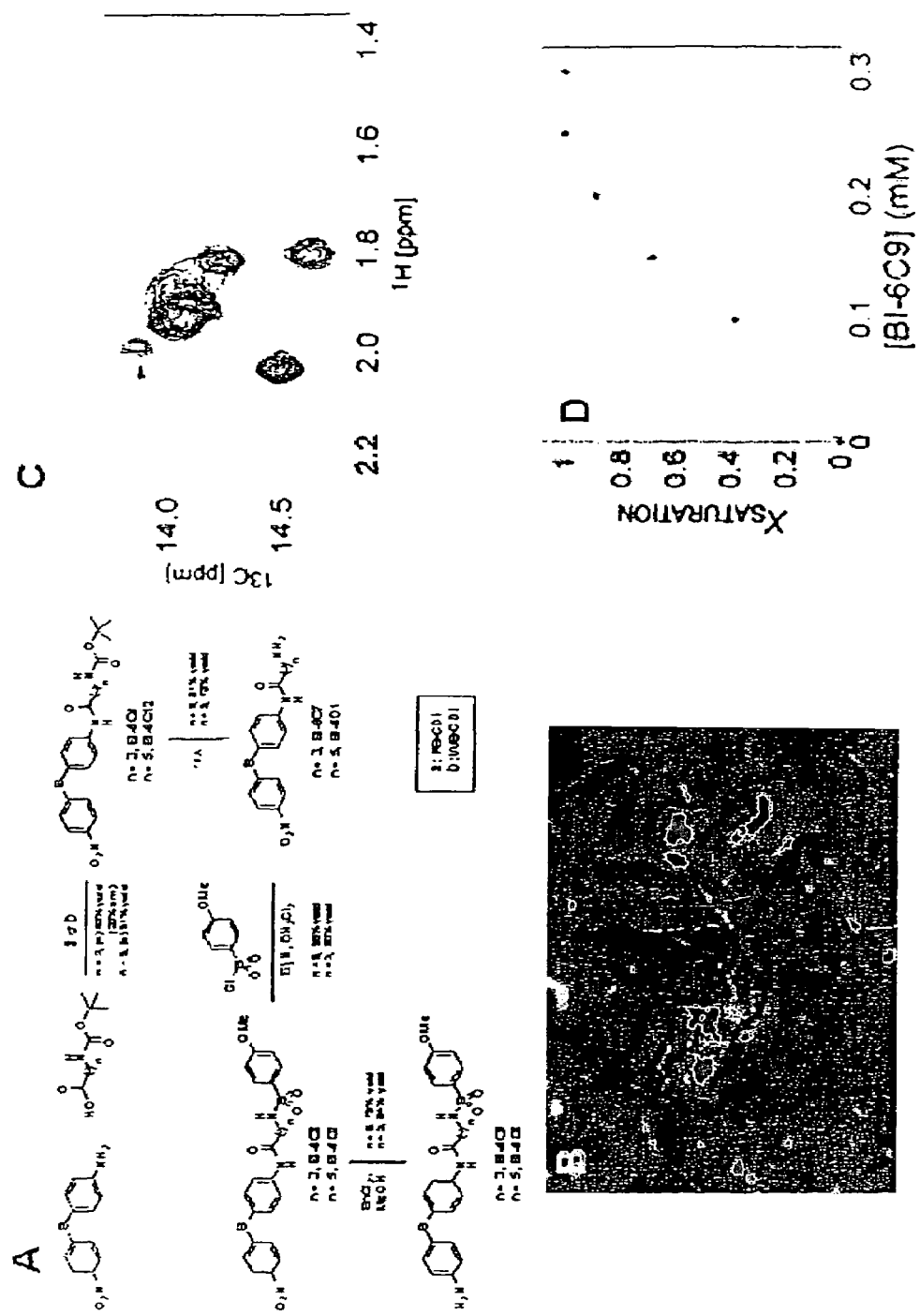
FIG. 5 provides a synthetic scheme that can be used to synthesize of a compound of the present invention, virtual docking of the compound of the present invention into the structure of BID, and NMR characterization of dislocation constant.
Figure 7:
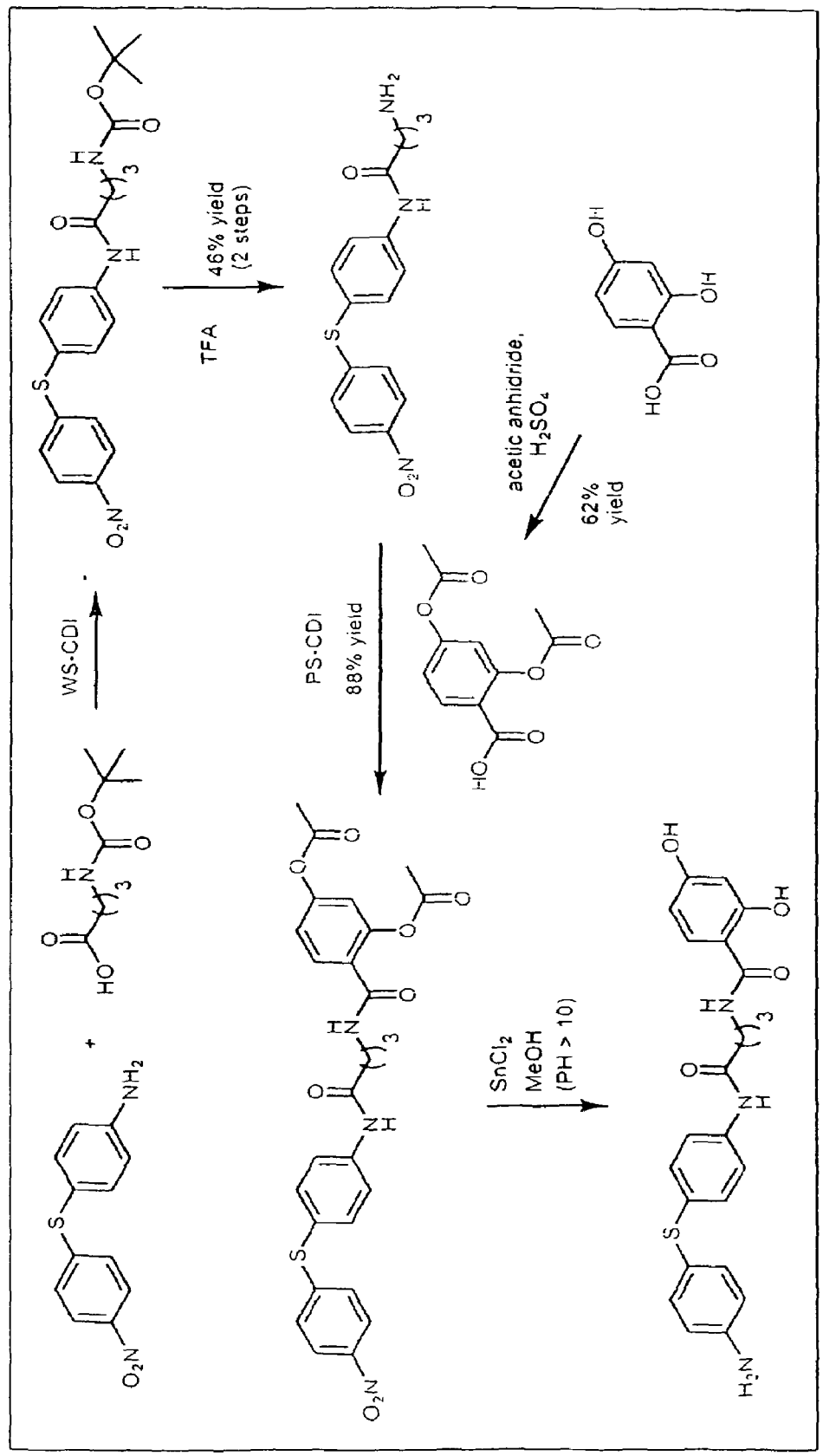
FIG. 7 illustrates a synthetic scheme for the synthesis of one compound of the present invention.

The synthesis of the title Compound I is shown schematically on FIGS. 5A and 7. Briefly, the formation of the peptide bond was aided by resin-bound carbodiimide, such as N-cyclohexylcarbodiimide-N'-propylmethyl polystyrene (PS-CDI) (available from) Argonaut Technologies) or 1-ethyl-3-(3-dimethylaminopropyl)carbodiimide hydrochloride (WS-CDI resin), using as starting materials the commercially available 4-amino-4'-nitrodiphenyl sulfide (available from Aldrich) and 4-[(tert-butoxycarbonyl)amino]butanoic acid (Boc-GABA-OH, available from Novabiochem). Stirring the reaction mixture at room temperature resulted in the corresponding Boc-protected amine (Compound VI, also shown above in the application). De-protection with trifluoroacetic acid (TFA) gave the free amine (Compound VII), with good yield. Following reaction with 4-methoxybenzenesulfonyl chloride afforded the corresponding sulfonamides in very high yields. The synthesis was completed by reducing the aromatic nitro group to the title Compound I, in presence of tin dichloride ($SnCl_2$).

The following spectral data was obtained for the title Compound I: $^1$H NMR (d-DMSO, 300 MHz): 10.06 (s, 1H), 9.92 (s, 1H), 8.58-8.56 (m, 1H), 7.90 (d, J=9 Hz, 1H), 7.68 (d, J=9 Hz, 1H), 7.49 (d, J=8.4 Hz, 2H), 7.14 (d, J=8.4 Hz, 2H), 7.03 (d, J=8.4 Hz, 2H), 6.59 (d, J=8.4, 2H), 6.30-6.22 (m, 2H), 5.46 (bs, 2H), 3.42-3.35 (m. 2H), 2.36-2.32 (m, 2H), 1.88-1.80 (m. 2H). MALDI-MS: 438 (15, M$^+$+1), 437 (10, M$^+$), 362 (20), 320 (35), 304 (30), 282 (95), 273 (100).

Example 3

Synthesis of {3-[4-(4-nitro-phenylsulfanyl)-phenylcarbamoyl]-propyl}-carbamic acid tert-butyl ester (Compound VI)

VI

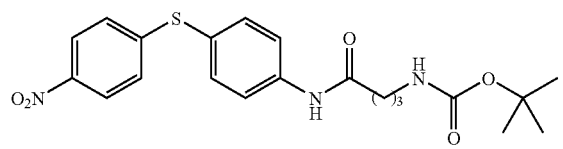

To synthesize the title Compound VI, PS-CDI resin described in Example 2 (730 mg, 1.0 mmol) was added to a dry round bottomed flask. t-Boc-4-aminobutanoic acid (152 mg, 0.75 mmol) was added as a solution in $CH_2Cl_2$ (4 ml) and the reaction mixture was stirred at room temperature. After 5 minutes, 4-amino-4'-nitrodiphenyl sulfide (123 mg, 0.5 mmol) in 4 ml of $CH_2Cl_2$ was added and the suspension stirred at room temperature for 4 days. The reaction mixture was filtered under vacuum and the resin was washed twice with $CH_2Cl_2$. Concentration of the filtrate afforded a crude that was purified by flash chromatography (hexane/ethyl acetate 1:1) to give the pure title Compound VI (274 mg, 64%) as a yellow solid, together with unreacted starting material (25 mg, 20%).

The following spectral data was obtained for the title Compound VI: $^1$H NMR (d-DMSO, 500 MHz): 10.19 (s, 1H), 8.13 (d, J=8.5 Hz, 2H), 7.78 (d, J=8.5 Hz, 2H), 7.55 (d, J=8.5 Hz, 2H), 7.23 (d, J=8.5 Hz, 2H), 3.00-2.97 (m, 2H), 2.37-2.34 (m, 2H), 1.73-1.70 (m, 2H), 1.39 (s, 9H). $^{13}$C NMR (d-DMSO, 125 MHz): 171.3, 155.6, 148.8, 144.7, 141.0, 135.9, 125.9, 124.2, 123.1, 121.7, 77.4, 33.8, 29.2, 28.2, 27.1.

Example 4

Synthesis of 4-amino-N-[4-(4-nitro-phenylsulfanyl)-phenyl]-butyramide (Compound VII)

VII

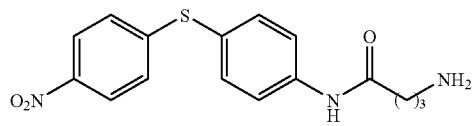

To synthesize the title Compound VII, Compound VI (274 mg, 0.63 mmol) synthesized as described in Example 3, was added to a round bottomed flask and cooled to 0° C. The minimum amount of trifluoroacetic acid needed to dissolve the compound was added and the solution stirred at room temperature for 5 additional minutes. The acid was evaporated using a rotary evaporator and the residue dissolved in $CH_2Cl_2$. The solution was extracted with a 1 M solution of $K_2CO_3$ and water. The organic phase was dried over $Na_2SO_4$ and concentrated under reduced pressure to give the crude title Compound VII (170 mg, 81%) as a bright yellow solid. The compound was used with no further purification.

The following spectral data was obtained for the title Compound VII: $^1$H NMR (d-DMSO, 500 MHz): 8.13 (d, J=6.0 Hz, 2H), 7.78 (d, J=9.5 Hz, 2H), 7.55 (d, J=6.0 Hz, 2H), 7.23 (d, J=9.5 Hz, 2H), 2.61-2.58 (m, 2H), 2.40-2.39 (m, 2H), 1.70-1.67 (m, 2H). $^{13}$C NMR (d-DMSO, 125 MHz): 171.9, 148.8, 144.7, 141.1, 135.9, 125.8, 124.2, 123.1, 121.7, 41.1, 34.1, 29.0.

Example 5

Synthesis of 4-(4-methoxy-benzenesulfonylamino)-N-[4-(4-nitro-phenylsulfanyl)-phenyl]-butyramide (Compound III)

III

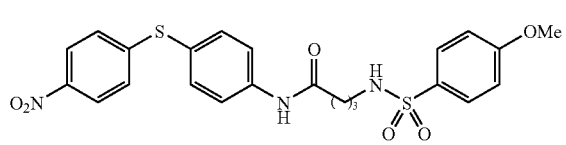

To synthesize the title Compound III, Compound VII (33 mg, 0.1 mmol) synthesized as described in Example 4, and triethylamine (13 mg, 0.13 mmol) in 1 ml of $CH_2Cl_2$ were cooled to 0° C. and 4-methoxybenzebesulfonyl chloride (23 mg, 0.11 mmol) was added as a solution in 1.5 ml of $CH_2Cl_2$. After stirring 2 hours at 0° C. and overnight at room temperature the reaction mixture was washed with water and a saturated solution of NaCl in water. The organic phase was dried over $Na_2SO_4$ and concentrated under reduced pressure to afford the title Compound III (48 mg, 96%) as a light yellow solid.

The following spectral data was obtained for the title Compound III: $^1$H NMR (d-DMSO, 500 MHz): 10.18 (s, 1H), 8.13 (d, J=9.0 Hz, 2H), 7.77-7.72 (m, 4H), 7.55 (d, J=8.5 Hz, 2H), 7.50 (t, J=6.0 Hz, 1H), 7.23 (d, J=9.0 Hz, 2H), 7.11 (d, J=8.5 Hz, 2H), 3.84 (s, 3H), 2.78-2.74 (m, 2H), 2.40-2.38 (m, 2H), 1.74-1.69 (m, 2H). $^{13}$C NMR (d-DMSO, 125 MHz): 171.0, 162.0, 159.6, 159.5, 159.3, 157.5, 148.8, 140.9, 132.0, 125.9, 124.2, 121.8, 114.2, 55.5, 41.9, 36.7, 32.0.

Example 6

Synthesis of N-[4-(4-amino-phenylsulfanyl)-phenyl]-4-(4-methoxy-benzenesulfonylamino)-butyramide (Compound II)

II

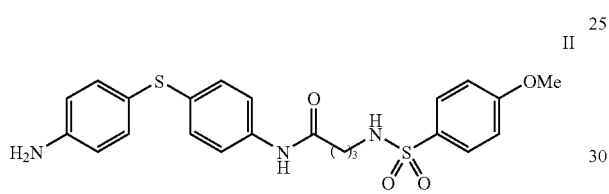

To synthesize the title Compound II, to Compound III (38 mg, 0.077 mmol) synthesized as described in Example 5, in 2 ml of MeOH, was added $SnCl_2$ (85 mg, 0.38 mmol) and the mixture was refluxed for 5 hours. Methanol was then evaporated and a solution 10% $NaHCO_3$ was added carefully at 0° C. The residue was extracted with ethyl acetate and the combined organic phases were dried over $Na_2SO_4$ and concentrated under reduced pressure to give the title Compound II (27 mg, 75%) as a dark yellow solid.

The following spectral data was obtained for the title Compound II: $^1$H NMR (d-DMSO, 500 MHz): 9.84 (s, 1H), 7.70 (d, J=9.0 Hz, 2H), 7.46-7.43 (m, 3H), 7.13-7.07 (m, 4H), 7.01 (d, J=8.5 Hz, 2H), 6.58 (d, J=9.0 Hz, 2H), 3.81 (s, 3H), 2.73-2.69 (m, 2H), 2.29-2.26 (m, 2H), 1.67-1.63 (m, 2H). $^{13}$C NMR (d-DMSO, 125 MHz): 170.4, 161.9, 149.4, 137.0, 135.3, 132.7, 131.9, 128.5, 127.8, 119.7, 116.4, 114.7, 114.2, 55.5, 42.0, 33.2, 24.8.

Example 7

Synthesis of {5-[4-(4-nitro-phenylsulfanyl)-phenyl-carbamoyl]-pentyl}-carbamic acid tert-butyl ester (Compound VIII)

VIII

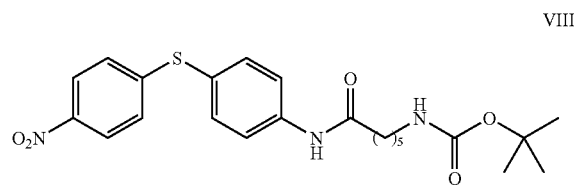

To synthesize the title Compound VIII, WS-CDI resin described in Example 2 (422 mg 2.2 mmol) was added to a solution of t-Boc-4-aminobutanoic acid (509 mg, 2.2 mmol), 4-amino-4'-nitrodiphenyl sulfide (493 mg, 2.0 mmol) and triethylamine (202 mg, 2.0 mmol) in $CH_2Cl_2$ (6 ml). After 12 hours stirring at room temperature, the reaction mixture was washed with water, 6 N HCl, water, saturated $NaHCO_3$ solution, and water. The organic layer was dried over $Na_2SO_4$ and the solvent evaporated under reduced pressure to give the title Compound VIII as a yellow solid (466 mg, 51%).

The following spectral data was obtained for the title Compound VIII: $^1$H NMR (d-DMSO, 500 MHz): 10.15 (s, 1H), 8.13 (d, J=8.2 Hz, 2H), 7.78 (d, J=5.8 Hz, 2H), 7.55 (d, J=5.8 Hz, 2H), 7.24 (d, J=8.2 Hz, 2H), 2.93-2.91 (m, 2H), 2.35-2.33 (m, 2H), 1.62-1.59 (m, 2H), 1.38 (s, 9H), 1.30-1.25 (m, 4H). $^{13}$C NMR (d-DMSO, 125 MHz): 171.6, 159.4, 155.5, 148.8, 144.7, 141.0, 135.9, 125.9, 124.2, 121.7, 77.2, 36.4, 29.2, 28.2, 25.9, 24.7.

Example 8

Synthesis of 6-amino-hexanoic acid [4-(4-nitro-phenylsulfanyl)-phenyl]-amide (Compound IX)

IX

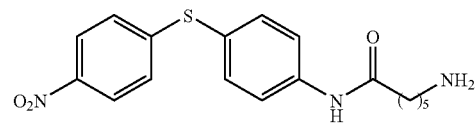

To synthesize the title Compound IX, Compound VIII (460 mg, 1.0 mmol) synthesized as described in Example 7, was added to a round bottomed flask and cooled to 0° C. The minimum amount of trifluoroacetic acid needed to dissolve the compound was added and the solution let under stirring at room temperature for 5 additional minutes. The acid was evaporated at the rotary evaporator and the residue dissolved in $CH_2Cl_2$. The solution was extracted with a 1 M solution of $K_2CO_3$ and water. The organic phase was dried over $Na_2SO_4$ and concentrated under reduced pressure to give the crude title Compound IX (280 mg, 78%) as a bright yellow solid. The compound was used for the following step with no further purification.

The following spectral data was obtained for the title Compound IX: $^1$H NMR (d-DMSO, 500 MHz): 10.16 (s, 1H), 8.13 (d, J=9.0 Hz, 2H), 7.78 (d, J=9.0 Hz, 2H), 7.55 (d, J=8.2 Hz, 2H), 7.24 (d, J=8.2 Hz, 2H), 2.56-2.54 (m, 2H), 2.37-2.36 (m, 2H), 1.63-1.60 (m, 2H), 1.39-1.34 (m, 4H). $^{13}$C NMR (d-DMSO, 125 MHz): 171.7, 148.8, 144.7, 141.1, 135.9, 125.8, 124.2, 123.1, 121.7, 41.4, 36.5, 32.8, 26.0, 24.9.

Example 9

Synthesis of 6-(4-methoxy-benzenesulfonylamino)-hexanoic acid [4-(4-nitro-phenylsulfanyl)-phenyl]-amide (Compound V)

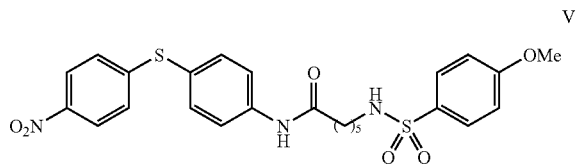

V

To synthesize the title Compound V, Compound IX (280 mg, 0.78 mmol) synthesized as described in Example 8, and triethylamine (132 mg, 1.0 mmol) in 5 ml of $CH_2Cl_2$ were cooled to 0 C and 4-methoxybenzebesulfonyl chloride (177 mg, 0.86 mmol) was added as a solution in 7 ml of $CH_2Cl_2$. After stirring 2 hours at 0° C. and overnight at room temperature the reaction mixture was washed with water and a saturated solution of NaCl in water. The organic phase was dried over $Na_2SO_4$ and concentrated under reduced pressure to afford the title Compound V (368 mg, 90%) as a light yellow solid.

The following spectral data was obtained for the title Compound V: $^1$H NMR (d-DMSO, 500 MHz): 10.14 (s, 1H), 8.13 (d, J=7.8 Hz, 2H), 7.79-7.72 (m, 4H), 7.54 (d, J=8.5 Hz, 2H), 7.23 (d, J=8.5 Hz, 2H), 7.11 (d, J=7.8, 2H), 3.84 (s, 3H), 2.72-2.70 (m, 2H), 2.33-2.30 (m, 2H), 1.55-1.28 (m, 6H). $^{13}$C NMR (d-DMSO, 125 MHz): 171.5, 161.9, 148.8, 144.7, 141.0, 135.8, 132.1, 125.9, 125.2, 124.1, 123.1, 121.7, 114.2, 55.5, 42.3, 36.3, 28.7, 25.7, 24.5.

Example 10

Synthesis of 6-(m-methoxy-benzenesulfonylamino)-hexanoic acid [4-(4-amino-phenylsulfanyl)-phenyl]-amide (Compound IV)

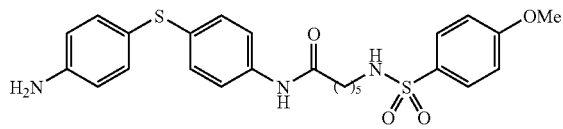

IV

To synthesize the title Compound IV, to a suspension of Compound V (100 mg, 0.19 mmol) synthesized as described in Example 9, in 4 ml of MeOH, was added $SnCl_2$ (213 mg, 0.94 mmol) and the mixture was refluxed for 5 hours. Methanol was then evaporated and a solution of 10% $NaHCO_3$ was added carefully at 0° C. The residue was extracted with ethyl acetate and the combined organic phases were dried over $Na_2SO_4$ and concentrated under reduced pressure to give the title Compound IV (80 mg, 84%) as a bright yellow solid.

The following spectral data was obtained for the title Compound IV: $^1$H NMR (d-DMSO, 500 MHz): 9.82 (s, 1H), 7.72 (d, J=7.0 Hz, 2H), 7.45 (d, J=7.0 Hz, 2H), 7.38 (bs, 1H), 7.14-7.02 (m, 6H), 6.60 (d, J=10.0 Hz, 2H), 5.42 (bs, 2H), 3.83 (s, 3H), 2.70-2.69 (m, 2H), 2.23 (bs, 2H), 1.51-1.25 (m, 6H). $^{13}$C NMR (d-DMSO, 125 MHz): 170.9, 161.9, 149.5, 137.1, 135.3, 132.7, 132.1, 127.8, 119.7, 116.3, 114.6, 114.4, 114.2, 55.5, 42.3, 36.1, 28.7, 25.7, 24.5.

Example 11

Intra- and Inter-Ligand Based Identification of Small Compounds that Bind BID

Figure 2:
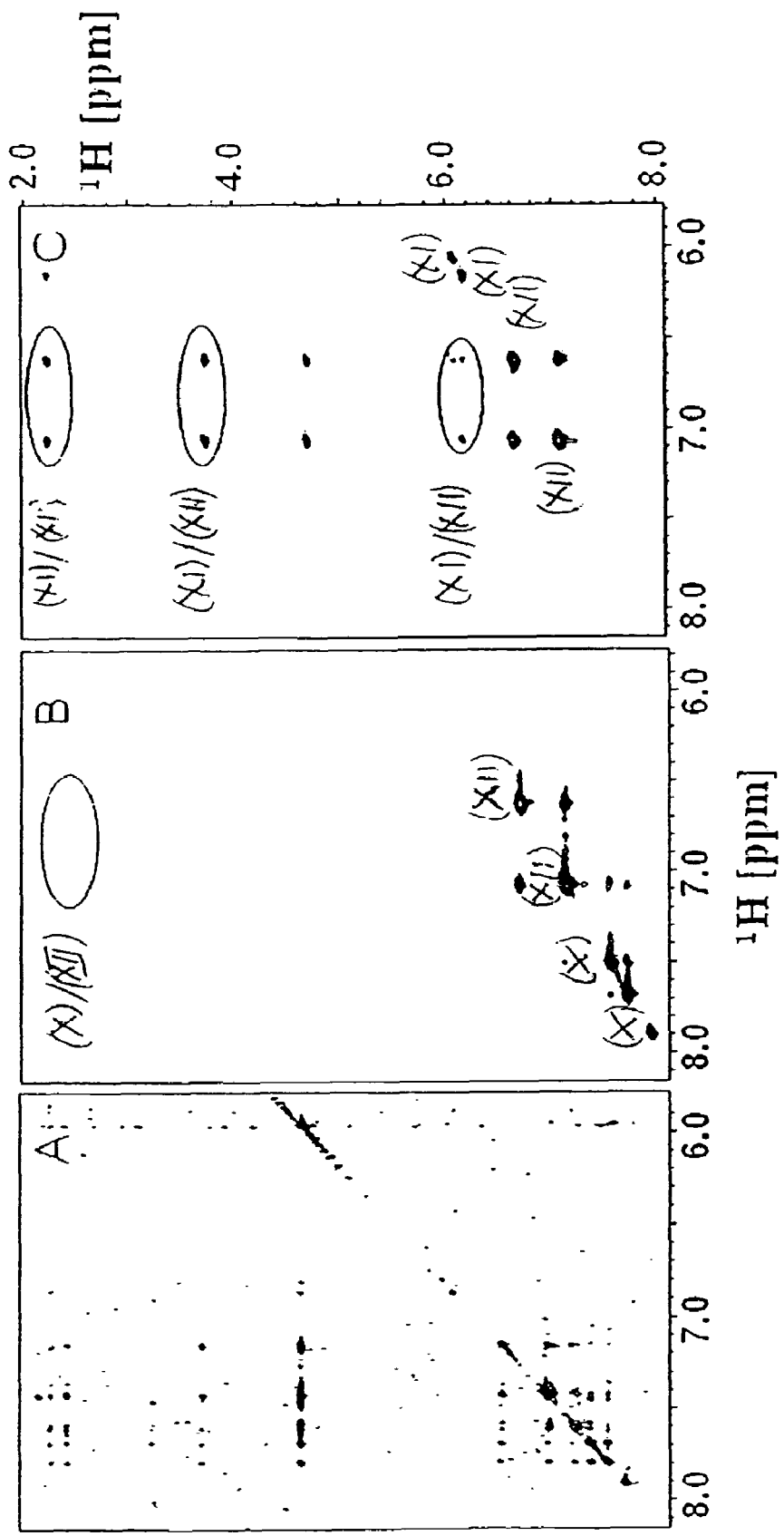
FIG. 2 demonstrates spectral intra- and inter-ligand based identification of some compounds that bind BID.

Several mixtures of compounds from the above-described library of scaffolds were prepared (0.4 to 0.9 mM each) and tested in presence of 10 μM BID (FIG. 2A). Typical trNOESY spectra were measured with 8 or 16 transients per increment with mixing times of 300 to 800 milliseconds, to maximize the detection of trNOEs and ILOEs. Pooling compounds in mixtures of 6 to 24, allowed the collection of the spectra for the 300 fragments library in a few days. Analysis of the data and subsequent deconvolution of the spectra allowed identification of weak ligands by means of positive trNOEs cross peaks. Similarly, compounds that bind BID in close proximity (less that 5 Å) are identified by detecting intermolecular NOEs (ILOEs) serving as building blocks for producing linked compounds. These compounds were compounds X-XII, the structures of which are shown below:

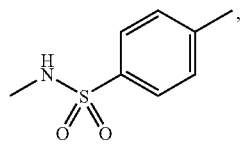

X

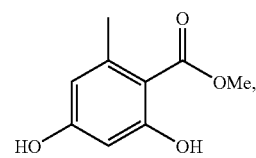

XI

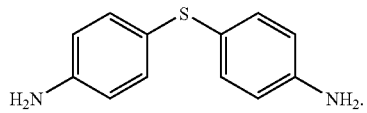

XII

As shown in FIGS. 2B and 2C, the experiments were repeated for the pairs that were recognized to bind to BID. Spectrum of a solution of compound (X)/compound (XII) in presence of BID (10 μM) is shown on FIG. 2B. Spectrum of a solution of compound (XI)/compound (XII) in presence of BID (10 μM) is shown on FIG. 2C. On FIG. 2C, ILOE cross-peaks between the two molecules are circled.

Figure 3:
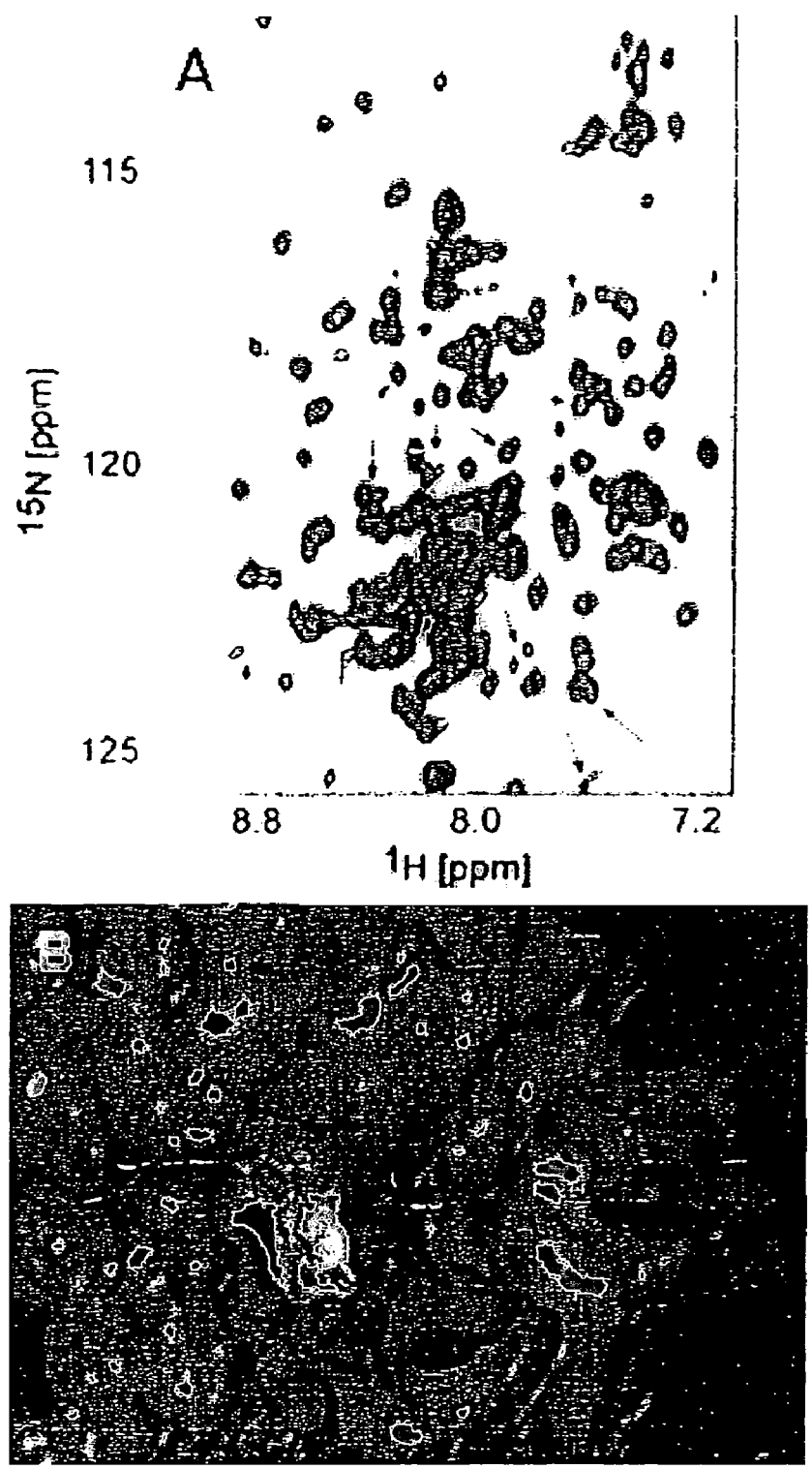
FIG. 3 provides microphotographs demonstrating binding to BID by chemical shift mapping.

To identify the amino acids involved in this interaction, 15N-labeled BID (0.5 mM) and acquired 2D [15N,1H]-TROSY spectra were prepared in absence and presence of compound (XII), which is a weak binder (FIG. 3A). As a result of the addition of compound (XII) to 15N-labeled BID several modification resulted in the [15N,1H]-TROSY spectrum of the protein and analysis of the chemical shift perturbations, based on the published resonances assignments, the interactions with the ligand were mapped. The residues mostly affected by this binding were S28, A87, L105, A137, G143, N144, K146, F171, L182, T185, S184. The changes were plotted on the three-dimensional structure of BID (PDB code 1DDB) and showed that most of the changes fall in proximity of the deep hydrophobic groove on the surface of the protein (FIG. 3B).

Once the interaction sites on the BID surface have been identified by chemical shift mapping, the two pairs of building blocks in the three-dimensional structure of the protein were docked to envisage possible linkers between the two fragments. The pair compound (X)/compound (XII) was examined. In silico docking by using FlexX as implemented in Sybyl (TRIPOS, Inc.) followed by CSCORE analysis and visual inspection was used. Several compounds that were docked are shown in Table 1 together with the fragments of compounds (X), (XI), and (XII). In Table 1, quantitative data is presented showing the test results for docking (fitting in the two sub-pockets, column 1), chemical shifts in HSQC spectra (NMR, column 2) and in vitro assays on isolated mitochondria (Smac release inhibition, column 3). Results are represented by plus and minus or by percentage of inhibition of Smac release.

TABLE 1

Qualitative Test Data for Compounds II-XII

| Compound | Structure | Fitting in the two sub-pockets | NMR binding | Smac release inhibition at 50 μM |
|---|---|---|---|---|
| XI | 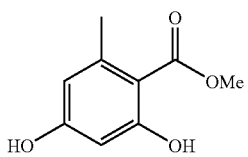 | ND*) | -**) | ND*) |
| X | 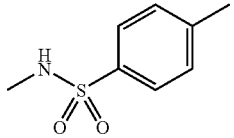 | ND*) | -**) | 0 |
| XII | 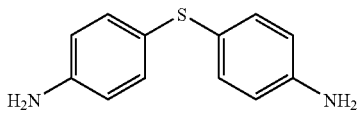 | + | + | 22 |
| VI | 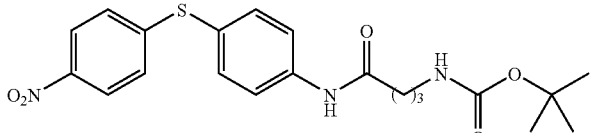 | ++ | ++ | 14 |
| VII | 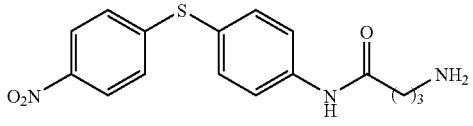 | ++ | + | 66 |
| III | 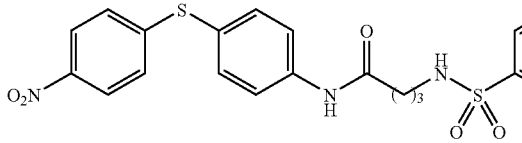 | ++++ | +++ | 24 |
| II | 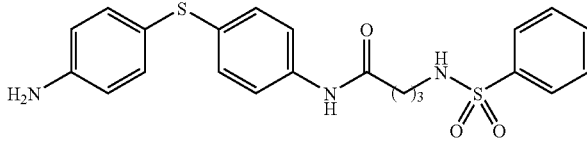 | +++ | ++++ | 100 |
| VIII | 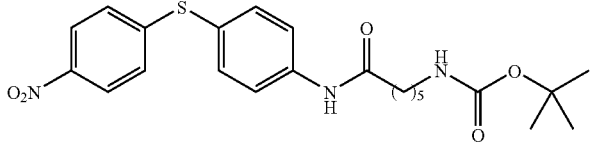 | ++ | ND*) | 0 |

TABLE 1-continued

Qualitative Test Data for Compounds II-XII

| Compound | Structure | Fitting in the two sub-pockets | NMR binding | Smac release inhibition at 50 μM |
|---|---|---|---|---|
| IX | O₂N–C₆H₄–S–C₆H₄–NH–C(O)–(CH₂)₅–NH₂ | ++ | ND*⁾ | 60 |
| V | O₂N–C₆H₄–S–C₆H₄–NH–C(O)–(CH₂)₅–NH–S(O)₂–C₆H₄–OMe | − | − | 16 |
| IV | H₂N–C₆H₄–S–C₆H₄–NH–C(O)–(CH₂)₅–NH–S(O)₂–C₆H₄–OMe | − | ND*⁾ | ND*⁾ |

*) Not determined.
**) iLOEs with compound (XII) were observed

Figure 4:
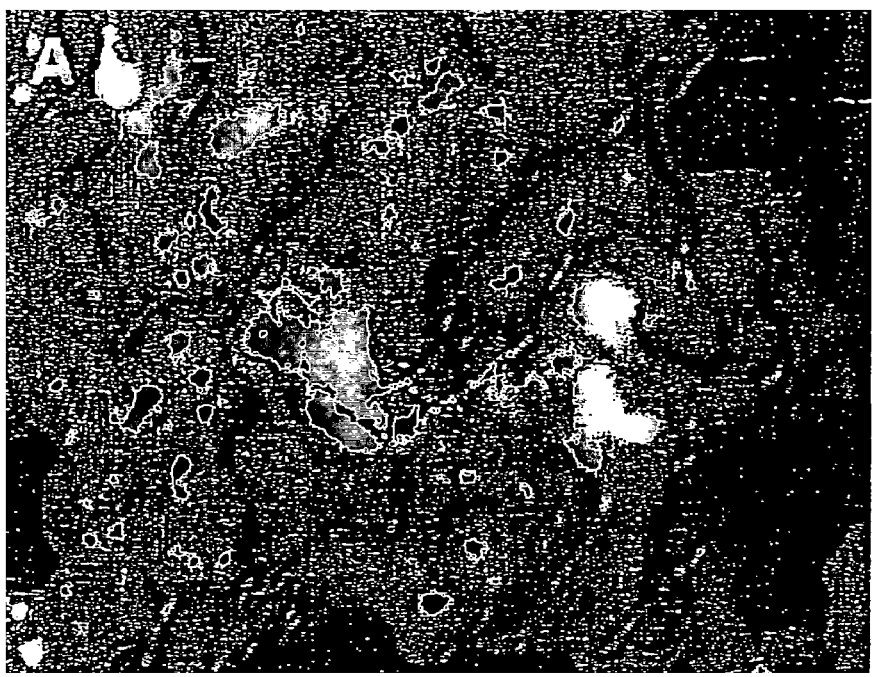
FIG. 4 provides microphotographs demonstrating virtual docking of a compound of the present invention into the three dimensional structure of BID.
Figure 4:

As shown by Table 1 and FIG. 4A, the best results in terms of fitting in the hydrophobic groove were observed for compounds III and II, while the corresponding 5-carbons linker derivatives did not dock well, thus identifying compounds II and III as best potential BID antagonists. Therefore, by using a combination of mixture-based trNOEs and ILOEs screening (SAR by ILOEs), chemical shift mapping, and virtual docking, a first series of bi-dentate compounds was designed targeting the hydrophobic groove near the BH3 region of BID (FIG. 4B).

Example 12

Study of Binding Activity of Some Compounds of the Invention to BID

To examine the binding affinity of some compounds of the invention to BID, 2D [¹³C,¹H]-HSQC spectra in presence of ¹³C methionine-labeled protein were measured, as at least one methionine is present in the hydrophobic groove of BID (FIG. 4B). FIG. 5B demonstrates docking of compound II into the three-dimensional structure of BID. FIG. 5C shows the 2D [¹³C,¹H]-HSQC spectrum of ¹³C methionine-labeled BID upon addition of 150 μM of compound II. The binding of compound II appears to be slow on the NMR-time scale, as indicated by the appearance/disappearance of cross-peaks in the spectrum upon titration (FIG. 5C).

Monitoring the variation of cross-peak intensity upon addition of increasing amounts of compound II, allowed to estimate its dissociation constant $K_D$. The arrow on FIG. 5C indicates the peak that was monitored to determine the $K_d$ for compound II. As shown by FIG. 5C, $K_D$~20 μM. FIG. 5D shows the plot of the peak volume versus the concentration of compound II. The peak volume was referenced to a peak that was unaffected by compound II and the peak volume was plotted as the fraction of the maximum peak volume observed for saturation of BID with compound II.

Chemical shift mapping using compound II and ¹⁵N-BID was also performed. Although the shifts are not very large presumably due to the limited solubility of the compound at the concentrations needed for such experiments, or because the complex may be in the slow to intermediate exchange with respect to ¹H and ¹⁵N resonances, larger and more evident effects were obtained with ¹⁵N-BID after cleavage with caspase-8, leading to tBID. This observation suggests that the truncated BID protein is capable of binding even better to compound II than full-length BID.

Example 13

In Vitro and Cell-Based Assaying

Figure 6:
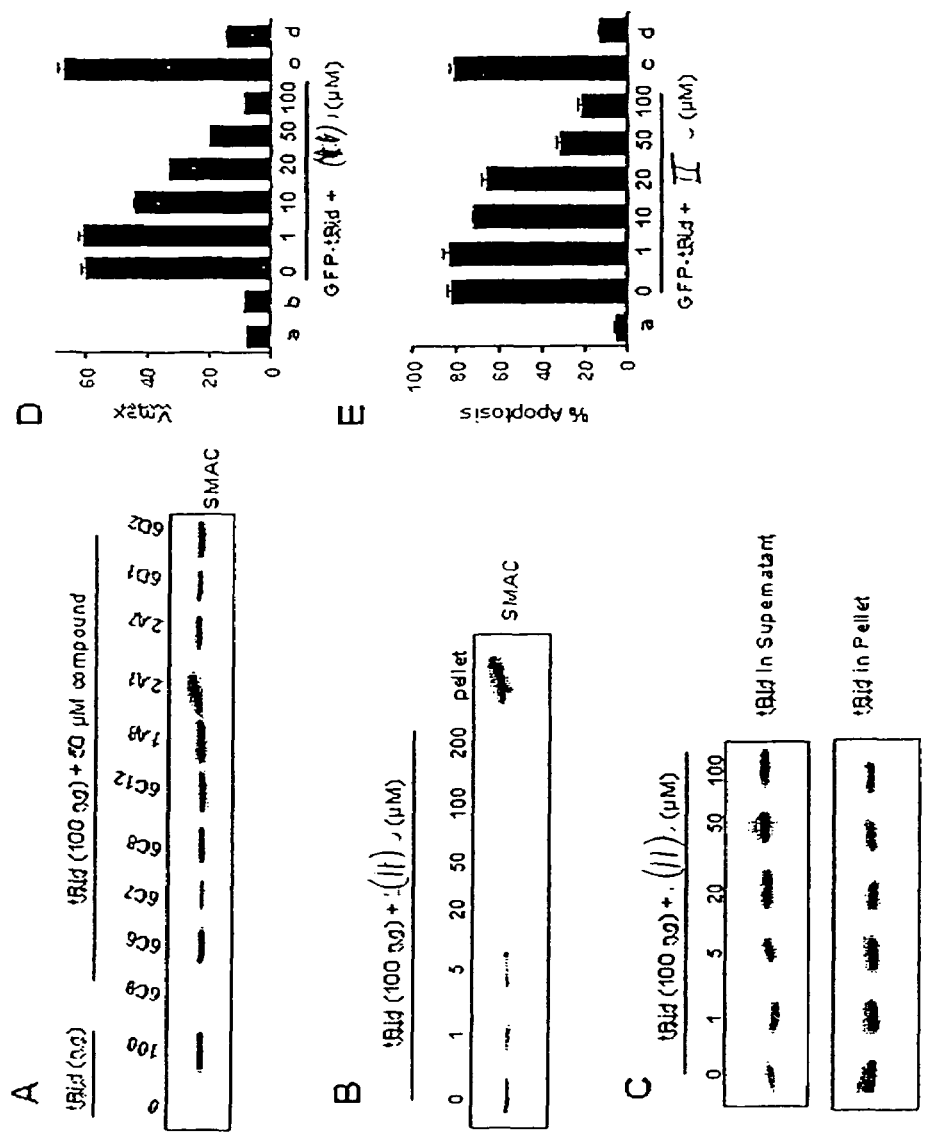
FIG. 6 illustrates suppression of tBID activity in vitro and in cells by BID-binding compounds.

Compounds II-IX were tested in vitro for their ability to inhibit BID-mediated release of Smac using mitochondria isolated from HeLa cells (FIG. 6A). The first lane represents mitochondria incubated without tBID. All others received 100 ng tBID without or with compounds. Each compound was tested at a concentration of 50 μM. As illustrated in FIG. 6A, only compound II was able to significantly reduce tBID-induced Smac release at this concentration. This compound was then tested at several doses using the same mitochondria-based assay, showing that it dramatically decreased Smac release at concentrations as low as 20 μM (FIG. 6B). To preliminarily investigate the mechanism by which compound II reduces Smac-release from isolated mitochondria, the tBID protein was treated with different concentrations of BI-6C9, after which it was incubated with mitochondria, followed by analysis of the bound and unbound fractions by immunoblotting using BID antibody. The concentration of mitochondria-bound tBID diminished in response to increasing concentrations of compound II. Dose-response experiments showed that the compound is effective at inhibiting tBID association with isolated mitochondria at 20 μM (FIG. 6C).

Compound II was also evaluated for its ability to inhibit BID-induced apoptosis in cell; for these experiments, HeLa cells were transfected with a plasmid encoding tBID, and effector caspase activity was measured in cell lysates 24 hours later. BI-6C9 reduced caspase-3 activity in tBID-transfected cells by ~4 fold at 50 □M, whereas caspase activity was totally blocked at 100 □M (FIG. 6D). Moreover, tBID-induced cell death, as measured by caspase-3 activity, was reduced from 80±5% to 35±5% by 50 □M of compound II (FIG. 6E). In FIGS. 6D and 6E, (a) is GFP; (b) is GFP+compound II (100 □M); (c) is GFP+compound III (100 □M); (d) is Z-VAD-fmk.

As a control study, it was verified that compound II does not bind appreciably to other BCL-2 family proteins such as BCL-$X_L$ (NMR-binding assay). Finally, it has been also determined that compound II does not impair caspase-8 mediated BID cleavage (by SDS page) and does not inhibit caspase-3 (in vitro assay) at the concentrations used in the cellular assay (not shown).

Example 14

Comparative Study of Activity

Figure 8:
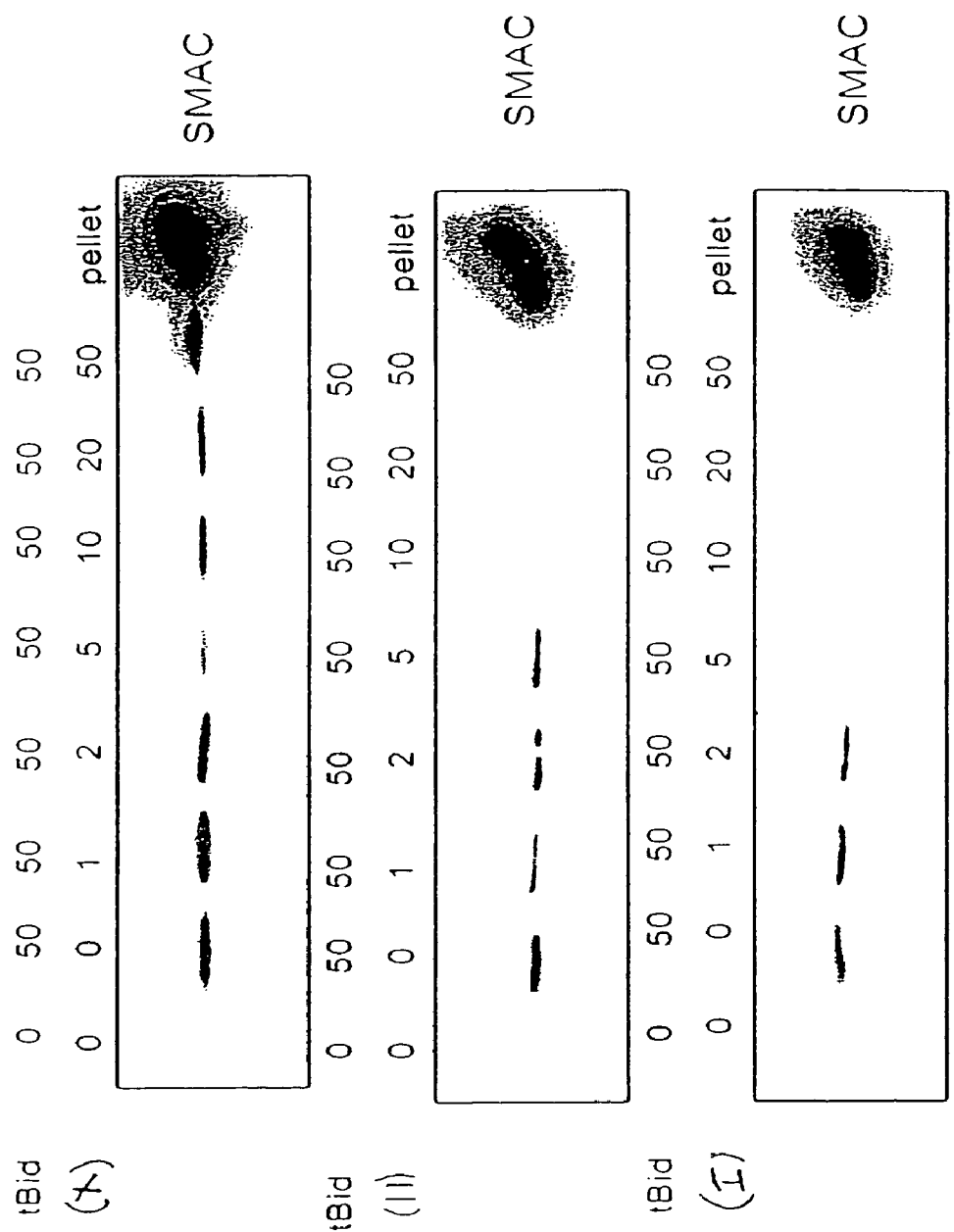
FIG. 8 demonstrates identification of compounds that bind BID.
Figure 9:
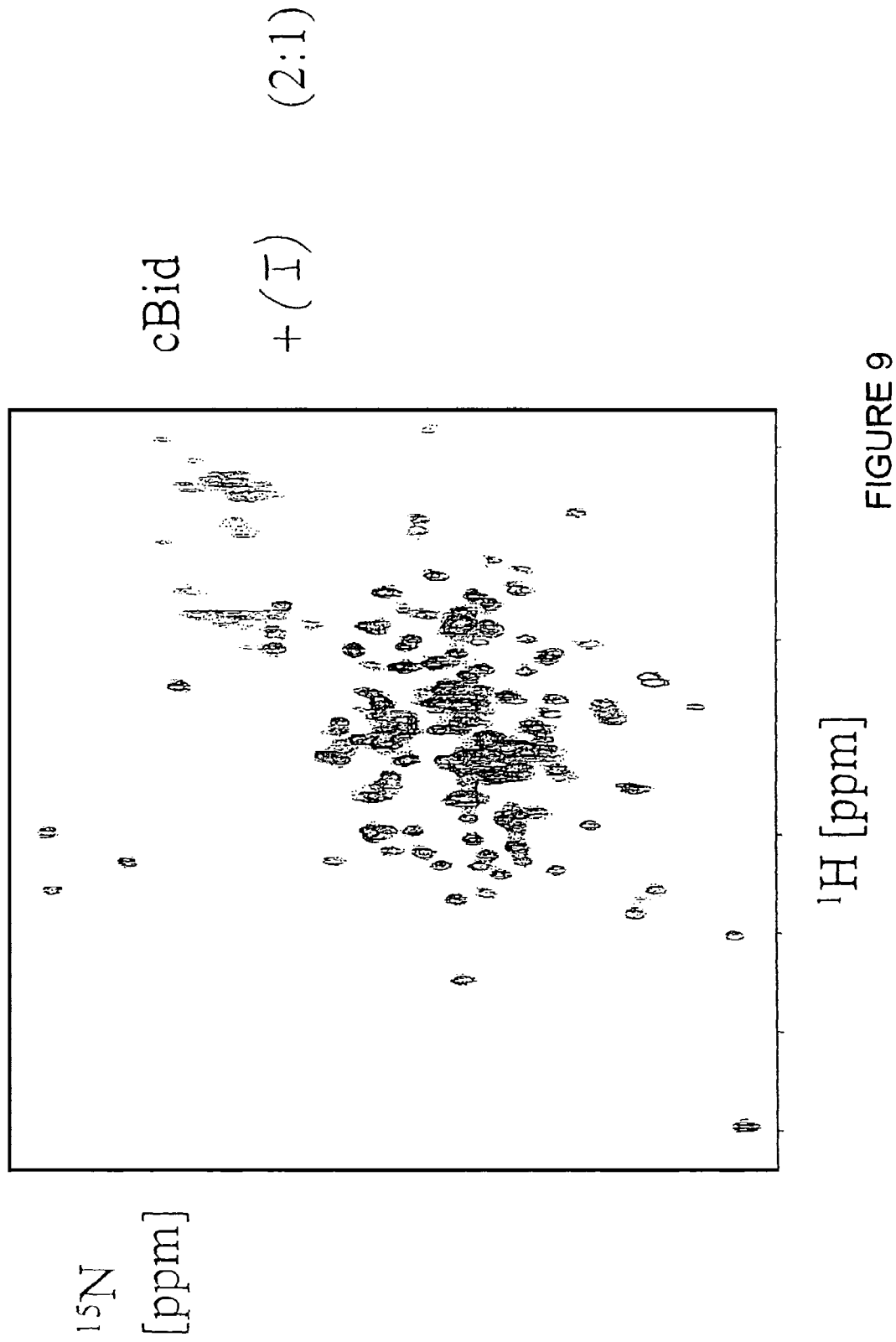
FIG. 9 demonstrates binding of one compound of the present invention to BID.

About 50 ng of tBID cleaved by cascade 8 was pre-incubated for about 15 minutes at about 30° C. with various concentrations of compounds I, II, and X. Then, about 50 μg of isolated mitochondria from Hela cells were added to the reaction system. After about 1 hour of incubation at about 30° C., the samples were centrifuged at 10,000×g for about 5 minutes at about 4° C., and the supernatant was analyzed by SDS-PAGE/immunoblotting using Smac antibody. The results of the analysis are presented on FIG. 8. As shown by FIG. 9, compound I is a strong binder for BID.

To conduct further comparative characterization of compounds I and II, 15N labeled BID was prepared and 2D [15N-1H]-TROSY spectra were obtained in absence or presence of compounds I and II. Upon addition of the compound, several chemical shift perturbations were observed, with compound I producing the largest shifts (not shown) compatible with specific binding in the low micromolar range. The shifts were larger when the protein is cleaved by caspase-8, signifying that compound I may bind to tBID with higher affinity.

Figure 10:
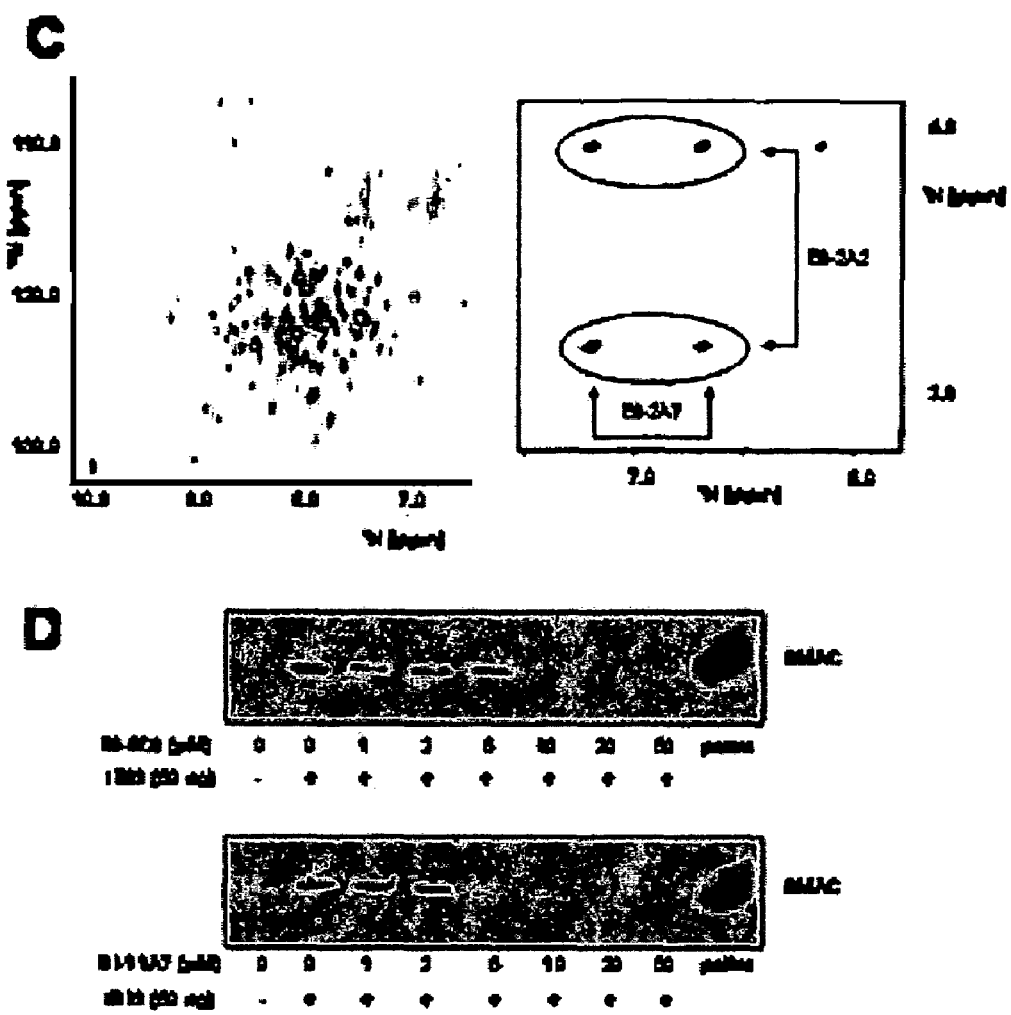
FIG. 10 demonstrates in vitro activity of some BID inhibitors of the present invention.

Some results of comparative studies of compounds I and II are shown on FIG. 10. The upper panel on FIG. 10 shows 2D [15N,1H]-TROSY spectrum measured with a sample of 0.5 mM tBID (obtained by cleavage of BID with caspase-8) in the absence and presence of 1 mM compound I. The lower panels on FIG. 10 show block tBID-induced Smac release of compounds I and II from mitochondria isolated from HeLa cells. The first lane represents mitochondria incubated without tBID. All others received 50 ng tBid without or with bi-dentate compound.

It is worth mentioning that when the compounds I and II were tested in a similar NMR-based assay against BCL-$x_L$, a pro-apoptotic member of the BCL-2 family with overall topology and structure that is similar to BID18, they did not show appreciable binding.

Example 15

Neuronal Cell-Based Evaluations

Figure 11:
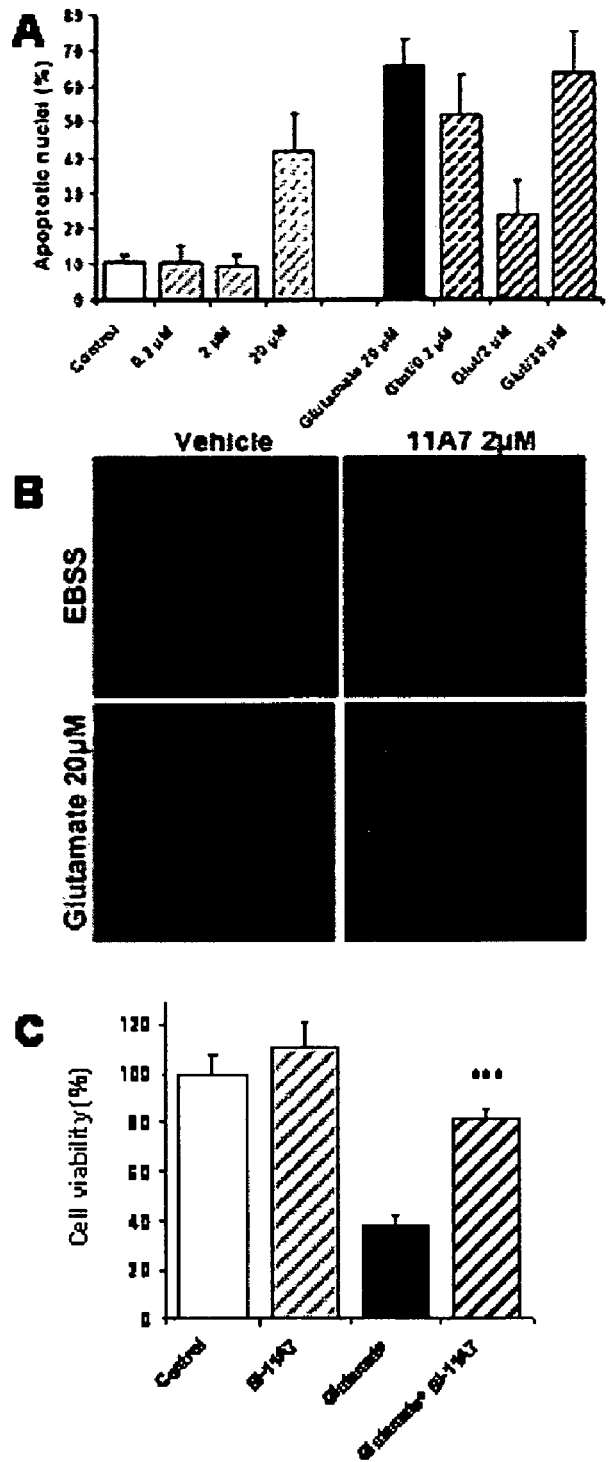
FIG. 11 demonstrates cell-based evaluation of BID inhibitors.

To assess whether the compounds of the present invention would also prevent neuronal cell death in primary cultures, a number of cell-based assays were performed. The results are shown by FIG. 11. Embryonic rat hippocampal (FIG. 11A) or cortical neurons (FIG. 11B) were pretreated with compound I at the indicated concentrations for 1 hour before exposure to glutamate (20 μM) in EBSS. Twenty-four hours later, apoptotic nuclei were quantified after staining with Hoechst 33342. In a separate experiment (FIG. 11C), the protective effect of Compound I against glutamate-induced cell death was quantified by the MTT assay. The graphs on FIG. 11 show mean percentages of apoptotic nuclei (FIG. 11A) or cell viability (FIG. 11C) and SD of 5 separate dishes per group. On FIG. 11C, the comparison is made to glutamate-treated cells (ANOVA, Scheffé test)(***, p<0.001). When tested against primary hippocampal neurons, compound I shows some toxicity at higher concentrations (20 μM) but it displays a good dose-dependent neuroprotective effect in the low micromolar range (0.2-2 μM, FIG. 11A). Similar results can be observed when using primary cortical neurons (FIGS. 11B and 11C).

Figure 12:
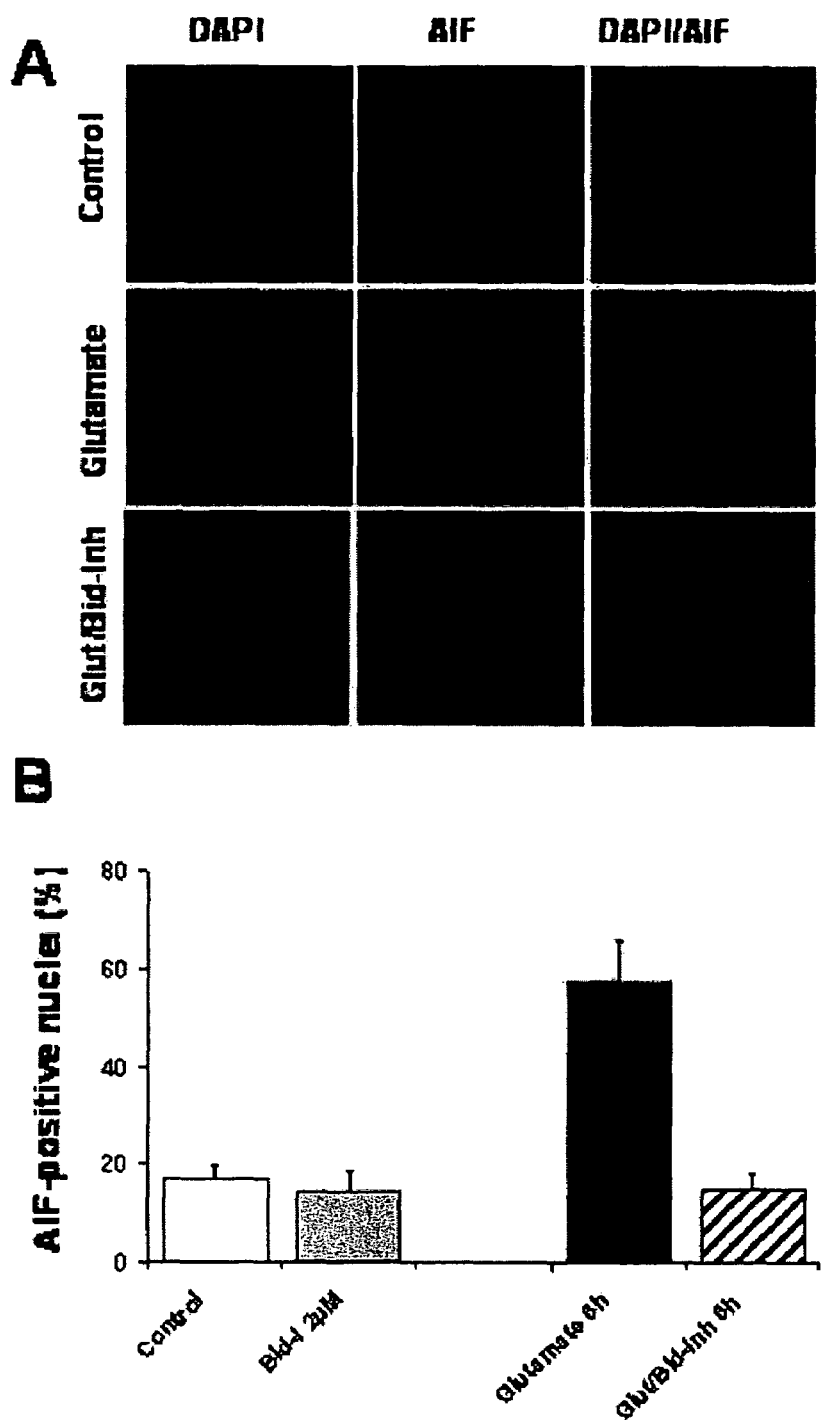
FIG. 12 demonstrates cell-based evaluation of BID inhibitors as related to primary neuronal cells.

FIG. 12 shows cell-based evaluation related to apoptosis inducing factor (AIF) and demonstrates that compound I also prevented nuclear translocation of AIF in neurons exposed to glutamate. Indeed, FIG. 12A shows, by immunostaining of rat embryonic cortical neurons, translocation of AIF (green fluorescence) to the nucleus 8 hours after exposure to glutamate. Pretreatment with Compound I preserves nuclear morphology (blue fluorescence, Hoechst 33342) and prevents AIF translocation. FIG. 12B shows quantification of AIF positive nuclei in rat embryonic neurons exposed to glutamate (20 μM) for 8 h. Mean values and SD of 4 dishes per group are presented.

Although the invention has been described with reference to the above examples, it will be understood that modifications and variations are encompassed within the spirit and scope of the invention. Accordingly, the invention is limited only by the following claims.

What is claimed is:

1. A compound having the formula (A):

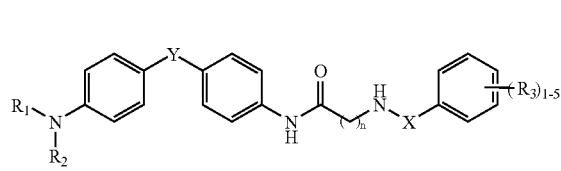

wherein each of $R_1$ and $R_2$ is independently selected from a group consisting of:

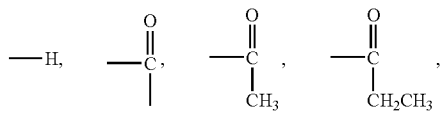

-continued

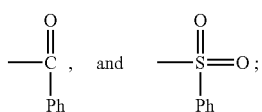

Y is a moiety selected from a group consisting of:

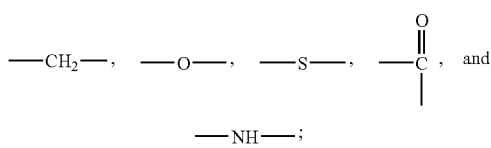

X is a moiety selected from a group consisting of:

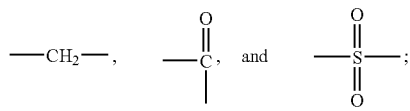

$R_3$ is at least one substituent in ortho-, meta-, or para-position of the benzene ring, wherein "$(R_3)_{1-5}$" symbolizes that the number of $R_3$ substitutents is between 1 and 5, inclusively, wherein $R_3$ is selected from a group consisting of:

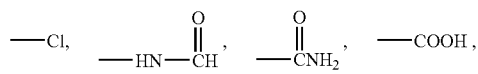

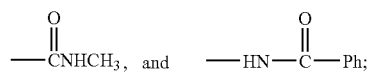

n is an integer having the value between 1 and 5; and

Ph in any of $R_1$, $R_2$, and $R_3$ is independently selected from an unsubstituted phenyl ring and a substituted phenyl ring having between one and five substitutents in ortho-, meta-, or para-position of the benzene ring, wherein the substitutents in the ring are selected from the group consisting of:

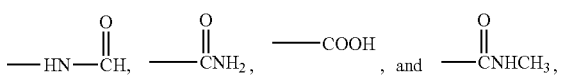

or a pharmaceutically acceptable salt thereof.

2. The compound of claim 1, having the formula (I):

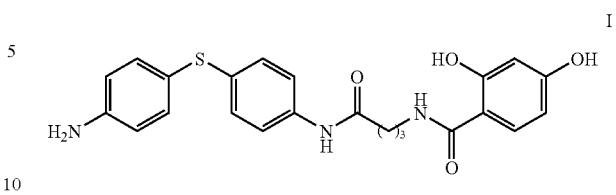

or a pharmaceutically acceptable salt thereof.

3. The compound of claim 1, having the formula II

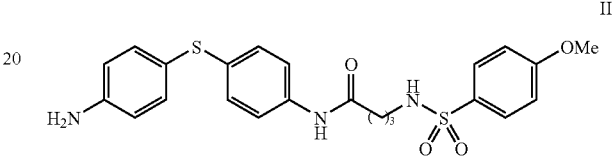

or a pharmaceutically acceptable salt thereof.

4. The compound of claim 1, having the formula III

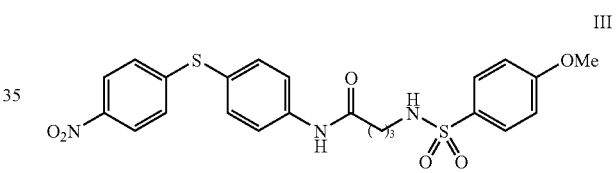

or a pharmaceutically acceptable salt thereof.

5. The compound of claim 1, having the formula IV

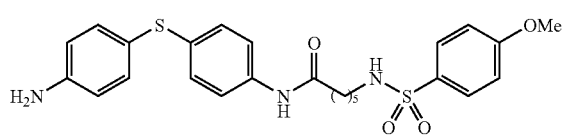

or a pharmaceutically acceptable salt thereof.

6. The compound of claim 1, having the formula V

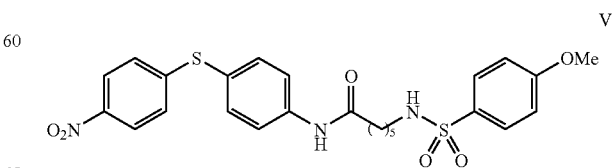

or a pharmaceutically acceptable salt thereof.

7. A compound having the formula C:

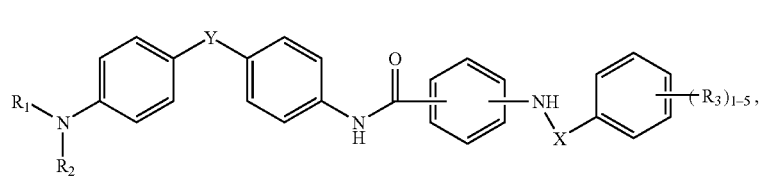

wherein each of $R_1$ and $R_2$ is independently selected from a group consisting of:

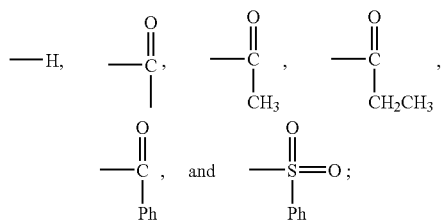

Y is a moiety selected from a group consisting of:

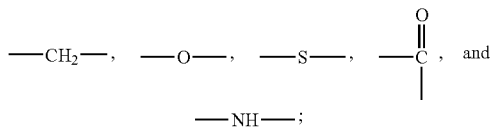

X is a moiety selected from a group consisting of:

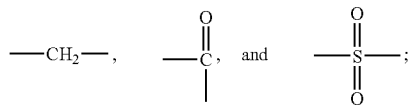

$R_3$ is at least one substitutent in ortho-, meta-, or para-position of the benzene ring, wherein "$(R_3)_{1-5}$" symbolizes that the number of $R_3$ substitutents is between 1 and 5, inclusively, wherein $R_3$ is selected from a group consisting of:

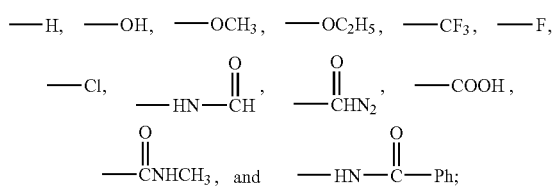

n is an integer having the value between 1 and 5; and

Ph in any of $R_1$, $R_2$, and $R_3$ is independently selected from an unsubstituted phenyl ring and a substituted phenyl ring having between one and five substitutents in ortho-, meta-, or para-position of the benzene ring, wherein the substitutents in the ring are selected from the group consisting of:

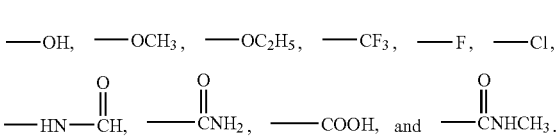

8. A pharmaceutical composition comprising at least one compound of claim 1 or 7, and a pharmaceutically acceptable carrier therefor.

* * * * *